(12) United States Patent
Belisle et al.

(10) Patent No.: US 12,214,562 B2
(45) Date of Patent: Feb. 4, 2025

(54) CARTRIDGE FOR VAPORIZER DEVICE

(71) Applicant: JUUL Labs, Inc., San Francisco, CA (US)

(72) Inventors: Christopher L. Belisle, Somerset, WI (US); Steven Christensen, San Mateo, CA (US); Eric Joseph Johnson, San Francisco, CA (US); Jason King, San Francisco, CA (US); James Monsees, San Francisco, CA (US); Matthew Rios, San Francisco, CA (US); Bryan White, Pleasanton, CA (US)

(73) Assignee: JUUL Labs, Inc., Washington, DC (US)

( * ) Notice: Subject to any disclaimer, the term of this patent is extended or adjusted under 35 U.S.C. 154(b) by 898 days.

(21) Appl. No.: 16/520,207

(22) Filed: Jul. 23, 2019

(65) Prior Publication Data

US 2020/0022418 A1    Jan. 23, 2020

Related U.S. Application Data

(60) Provisional application No. 62/702,326, filed on Jul. 23, 2018.

(51) Int. Cl.
| | |
|---|---|
| *A24F 47/00* | (2020.01) |
| *B29C 65/16* | (2006.01) |
| *B29C 70/88* | (2006.01) |
| *B29L 31/00* | (2006.01) |

(52) U.S. Cl.
CPC ............. *B29C 70/88* (2013.01); *A24F 47/00* (2013.01); *B29C 65/16* (2013.01); *B29K 2995/0025* (2013.01); *B29K 2995/0029* (2013.01); *B29L 2031/7414* (2013.01)

(58) Field of Classification Search
CPC ........ A24F 47/008; B29C 70/88; B29C 65/16
See application file for complete search history.

(56) References Cited

U.S. PATENT DOCUMENTS

| | | | |
|---|---|---|---|
| 7,793,861 B2 | 9/2010 | Bankers et al. |
| 8,833,364 B2 | 9/2014 | Buchberger |
| 8,991,402 B2 | 3/2015 | Bowen et al. |
| 9,247,773 B2 | 2/2016 | Memari et al. |
| 9,345,541 B2 | 5/2016 | Greeley et al. |
| 9,526,273 B2 | 12/2016 | Liu |
| 9,609,893 B2 | 4/2017 | Novak, III et al. |
| 9,675,109 B2 | 6/2017 | Monsees et al. |

(Continued)

FOREIGN PATENT DOCUMENTS

| | | |
|---|---|---|
| CN | 101843368 A | 9/2010 |
| CN | 201750712 U | 2/2011 |

(Continued)

*Primary Examiner* — Mathieu D Vargot
(74) *Attorney, Agent, or Firm* — Mintz Levin Cohn Ferris Glovsky and Popeo, P.C.

(57) ABSTRACT

A vaporizer cartridge is described that is configured for coupling to a vaporizer device body and containing a vaporizable material. Various embodiments of the vaporizer cartridge are described that include one or more features for maximizing a reservoir volume within the vaporizer cartridge for the containing of vaporizable material thereby increasing the output of vaporized vaporizable material from a compact cartridge configuration. Additionally, associated methods of manufacturing are described.

18 Claims, 5 Drawing Sheets

(56) References Cited

U.S. PATENT DOCUMENTS

| | | |
|---|---|---|
| 9,801,413 B2 | 10/2017 | Zhu |
| 9,814,265 B2 | 11/2017 | Rinker et al. |
| 10,092,713 B2 | 10/2018 | Terry et al. |
| 10,143,233 B2 | 12/2018 | Dubief et al. |
| 2005/0235991 A1 | 10/2005 | Nichols et al. |
| 2011/0277756 A1 | 11/2011 | Terry et al. |
| 2013/0319438 A1 | 12/2013 | Liu |
| 2014/0224244 A1 | 8/2014 | Liu |
| 2014/0261408 A1 | 9/2014 | Depiano et al. |
| 2014/0270729 A1 | 9/2014 | Depiano et al. |
| 2014/0270730 A1 | 9/2014 | Depiano et al. |
| 2014/0373857 A1 | 12/2014 | Steinberg |
| 2014/0376895 A1 | 12/2014 | Han |
| 2015/0020831 A1 | 1/2015 | Weigensberg et al. |
| 2015/0027471 A1 | 1/2015 | Feldman et al. |
| 2015/0078735 A1 | 3/2015 | Cormack |
| 2015/0114409 A1 | 4/2015 | Brammer et al. |
| 2015/0118895 A1 | 4/2015 | Zheng et al. |
| 2015/0136124 A1 | 5/2015 | Aronie et al. |
| 2015/0196060 A1 | 7/2015 | Wensley et al. |
| 2015/0208729 A1 | 7/2015 | Monsees et al. |
| 2015/0217068 A1 | 8/2015 | Wakalopulos |
| 2015/0245665 A1 | 9/2015 | Memari et al. |
| 2015/0335071 A1 | 11/2015 | Brinkley et al. |
| 2016/0044962 A1 | 2/2016 | Thorens et al. |
| 2016/0366941 A1* | 12/2016 | Lin .................. F16B 21/06 |
| 2016/0366947 A1 | 12/2016 | Monsees et al. |
| 2017/0231282 A1 | 8/2017 | Bowen et al. |
| 2017/0233114 A1* | 8/2017 | Christensen ............. B65B 3/14 141/2 |
| 2018/0027879 A1 | 2/2018 | Gavrielov et al. |
| 2018/0077967 A1 | 3/2018 | Hatton et al. |

FOREIGN PATENT DOCUMENTS

| | | |
|---|---|---|
| CN | 201781984 U | 4/2011 |
| CN | 202456410 U | 10/2012 |
| CN | 203072896 U | 7/2013 |
| CN | 203168033 U | 9/2013 |
| CN | 204120231 U | 1/2015 |
| CN | 204180941 U | 3/2015 |
| CN | 204905326 U | 12/2015 |
| CN | 205597123 U | 9/2016 |
| EP | 2614731 A1 | 7/2013 |
| KR | 20120132004 A | 12/2012 |
| WO | WO-2011146174 A2 | 11/2011 |
| WO | WO-2014150979 A2 | 9/2014 |
| WO | WO-2015149368 A1 | 10/2015 |
| WO | WO-2015168912 A1 | 11/2015 |
| WO | WO-2016005533 A1 | 1/2016 |
| WO | WO-2016092261 A1 | 6/2016 |
| WO | WO-2016122417 A1 | 8/2016 |
| WO | WO-2018029186 A1 | 2/2018 |

* cited by examiner

- - PRIOR ART - -

- - PRIOR ART - - ature may be opaque. The second part may define a mouthpiece of the vaporizer cartridge. The first part may include a stepped portion defining a stop feature along the reservoir housing. The stop feature may be shaped to prevent insertion of the vaporizer cartridge into a vaporizer body past the stepped portion. The stop feature may include an increase in a cross section of the reservoir housing. The wall thickness of the vaporizer cartridge may be substantially the same along the reservoir housing and the mouthpiece.

CARTRIDGE FOR VAPORIZER DEVICE

CROSS REFERENCE

The present application claims priority to U.S. Provisional Patent Application No. 62/702,326 entitled "Cartridge for Vaporizer Device" filed Jul. 23, 2018, which is hereby incorporated by reference in its entirety.

TECHNICAL FIELD

The subject matter described herein relates to vaporizer devices, including a disposable vaporizer cartridge.

BACKGROUND

Vaporizer devices, which can also be referred to as vaporizers, electronic vaporizer devices or e-vaporizer devices, can be used for delivery of an aerosol (or "vapor") containing one or more active ingredients by inhalation of the aerosol by a user of the vaporizing device. For example, electronic nicotine delivery systems (ENDS) include a class of vaporizer devices that are battery powered and that may be used to simulate the experience of smoking, but without burning of tobacco or other substances.

In use of a vaporizer device, the user inhales an aerosol, commonly called vapor, which may be generated by a heating element that vaporizes (e.g., causing a liquid or solid to at least partially transition to the gas phase) a vaporizable material, which may be liquid, a solution, a solid, a wax, or any other form as may be compatible with use of a specific vaporizer device. The vaporizable material used with a vaporizer can be provided within a cartridge (e.g., a separable part of the vaporizer that contains the vaporizable material in a reservoir) that includes a mouthpiece (e.g., for inhalation by a user).

To receive the inhalable aerosol generated by a vaporizer device, a user may, in certain examples, activate the vaporizer device by taking a puff, by pressing a button, or by some other approach. A puff, as the term is generally used (and also used herein), refers to inhalation by the user in a manner that causes a volume of air to be drawn into the vaporizer device such that the inhalable aerosol is generated by a combination of vaporized vaporizable material with the air.

The term vaporizer device, as used herein consistent with the current subject matter, generally refers to portable, self-contained, devices that are convenient for personal use. Typically, such devices are controlled by one or more switches, buttons, touch sensitive devices, or other user input functionality or the like (which can be referred to generally as controls) on the vaporizer, although a number of devices that may wirelessly communicate with an external controller (e.g., a smartphone, a smart watch, other wearable electronic devices, etc.) have recently become available. Control, in this context, refers generally to an ability to influence one or more of a variety of operating parameters, which may include without limitation any of causing the heater to be turned on and/or off, adjusting a minimum and/or maximum temperature to which the heater is heated during operation, various games or other interactive features that a user might access on a device, and/or other operations.

Various vaporizable materials having a variety of contents and proportions of such contents can be contained in the cartridge. Some vaporizable materials, for example, may have a smaller percentage of active ingredients per total volume of vaporizable material, such as due to regulations requiring certain active ingredient percentages. As a result, a user may need to vaporize a large amount of vaporizable material (e.g., compared to the overall volume of vaporizable material that can be stored in a cartridge) to achieve a desired effect.

SUMMARY

Aspects of the current subject matter relate to methods and system for a vaporizer cartridge and related methods of manufacturing. In one aspect, a method of manufacturing a vaporizer cartridge is described. The method may include filling a first part of a volume of a mold with a first material with the volume defining the vaporizer cartridge, and filling a second part of the volume with a second material.

In some variations, one or more of the following features can optionally be included in any feasible combination. The first part may define a reservoir housing of the vaporizer cartridge. The first material may be translucent and/or the second material may be opaque. The second part may define a mouthpiece of the vaporizer cartridge. The first part may include a stepped portion defining a stop feature along the reservoir housing. The stop feature may be shaped to prevent insertion of the vaporizer cartridge into a vaporizer body past the stepped portion. The stop feature may include an increase in a cross section of the reservoir housing. The wall thickness of the vaporizer cartridge may be substantially the same along the reservoir housing and the mouthpiece.

In some embodiments, the method may further include filling a second mold with a third material, and the second mold may define an air tube assembly. The method may further include laser welding the air tube assembly to at least one of the reservoir housing and the mouthpiece. The method may further include coupling a seal to a port of the air tube assembly thereby fluidically sealing a reservoir volume in the reservoir housing. The method may further include delivering a vaporizable material to the reservoir volume. The method may further include curing the first material and the second material, and laser welding a first end of the first part to a second end of the second part.

In another interrelated aspect of the current subject matter, a vaporizer cartridge for coupling to a vaporizer body to form a vaporizer device is described. The cartridge may include a reservoir housing defining a reservoir chamber for containing a vaporizable material and a mouthpiece coupled to the reservoir housing. The cartridge may further include an air tube assembly, which may include a wick housing portion configured to position a wicking element and a heating element in a vaporization chamber for vaporizing the vaporization material in the vaporization chamber. The air tube assembly may further include a tubing portion including a part of an airflow pathway that extends through the vaporization chamber and the mouthpiece thereby allowing vaporized vaporizable material to be inhaled by a user. Additionally, the cartridge may further include a filter housing portion configured to position a filter adjacent the mouthpiece.

In some embodiments, the air tube assembly may be made out of a single molded part. The tubing portion may be made out of metal. The filter housing and the wick housing may be made out of a plastic material.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

When practical, similar reference numbers denote similar structures, features, or elements.

DETAILED DESCRIPTION

Implementations of the current subject matter include devices relating to vaporizing of one or more materials for inhalation by a user. The term "vaporizer" is used generically in the following description to refer to a vaporizer device. Examples of vaporizers consistent with implementations of the current subject matter include electronic vaporizers or the like. Such vaporizers are generally portable, hand-held devices that heat a vaporizable material to provide an inhalable dose of the material.

In some vaporizer cartridge embodiments, an overlapping section forms between the reservoir and the mouthpiece. For example, approaches for coupling the reservoir to the mouthpiece may typically involve a snap-over coupling, a press-fit coupling, welding, or the like. As a result, the cartridge includes an overlapping section that may limit a volume of vaporizable material the cartridge can hold relative to the overall volume of the cartridge. For example, a cartridge that is 6 mm thick overall with an overlapping section including two 0.5 mm wall thickness decreases the vaporizable material volume capacity by 25%.

The vaporizable material used with a vaporizer may optionally be provided within a cartridge (e.g., a part of the vaporizer that contains the vaporizable material in a reservoir or other container and that can be refillable when empty or disposable in favor of a new cartridge containing additional vaporizable material of a same or different type). A vaporizer may be a cartridge-using vaporizer, a cartridge-less vaporizer, or a multi-use vaporizer capable of use with or without a cartridge. For example, a multi-use vaporizer may include a heating chamber (e.g., an oven) configured to receive a vaporizable material directly in the heating chamber and also to receive a cartridge or other replaceable device having a reservoir, a volume, or the like for at least partially containing a usable amount of vaporizable material.

In various implementations, a vaporizer may be configured for use with liquid vaporizable material (e.g., a carrier solution in which an active and/or inactive ingredient(s) are suspended or held in solution or a neat liquid form of the vaporizable material itself) or a solid vaporizable material. A solid vaporizable material may include a plant material that emits some part of the plant material as the vaporizable material (e.g., such that some part of the plant material remains as waste after the vaporizable material is emitted for inhalation by a user) or optionally can be a solid form of the vaporizable material itself (e.g., a "wax") such that all of the solid material can eventually be vaporized for inhalation. A liquid vaporizable material can likewise be capable of being completely vaporized or can include some part of the liquid material that remains after all of the material suitable for inhalation has been consumed.

Figure 1:
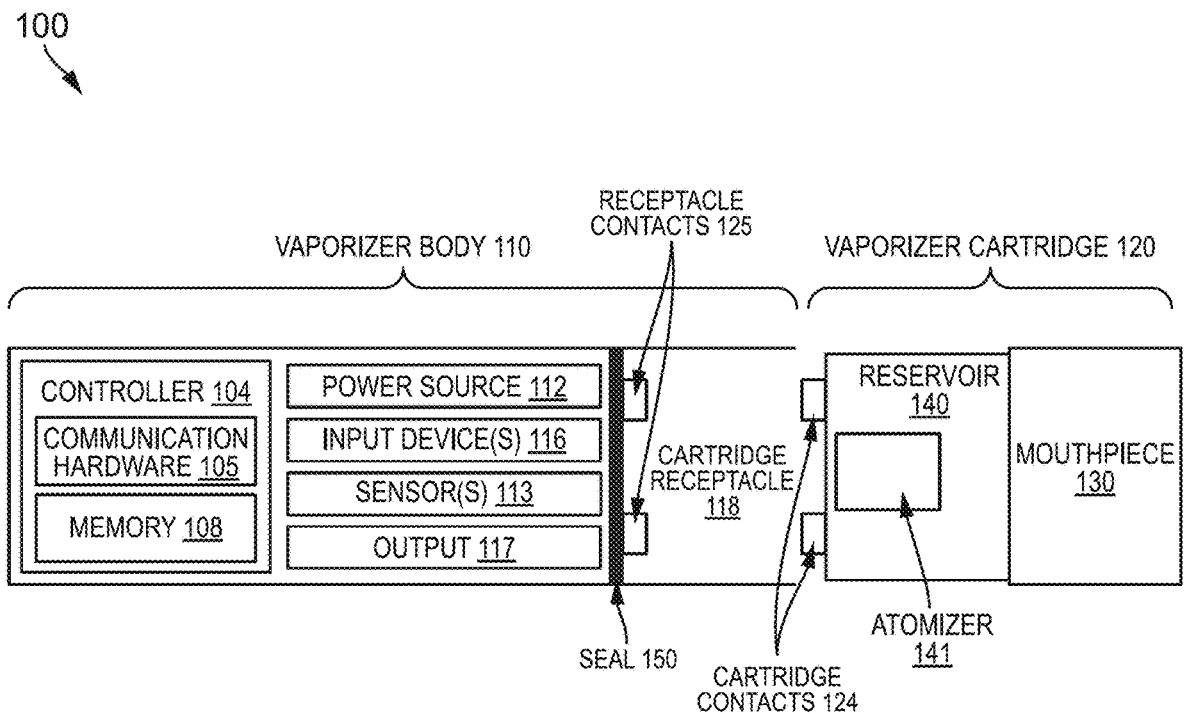
FIG. 1 illustrates a block diagram of a vaporizer consistent with implementations of the current subject matter.

Referring to the block diagram of FIG. 1, a vaporizer 100 typically includes a power source 112 (such as a battery which may be a rechargeable battery), and a controller 104 (e.g., a processor, circuitry, etc. capable of executing logic) for controlling delivery of heat to an atomizer 141 to cause a vaporizable material to be converted from a condensed form (e.g., a solid, a liquid, a solution, a suspension, a part of an at least partially unprocessed plant material, etc.) to the gas phase. The controller 104 may be part of one or more printed circuit boards (PCBs) consistent with certain implementations of the current subject matter.

After conversion of the vaporizable material to the gas phase, and depending on the type of vaporizer, the physical and chemical properties of the vaporizable material, and/or other factors, at least some of the gas-phase vaporizable material may condense to form particulate matter in at least a partial local equilibrium with the gas phase as part of an aerosol, which can form some or all of an inhalable dose provided by the vaporizer 100 for a given puff or draw on the vaporizer. It will be understood that the interplay between gas and condensed phases in an aerosol generated by a vaporizer can be complex and dynamic, as factors such as ambient temperature, relative humidity, chemistry, flow conditions in airflow paths (both inside the vaporizer and in the airways of a human or other animal), mixing of the gas-phase or aerosol-phase vaporizable material with other air streams, etc. may affect one or more physical parameters of an aerosol. In some vaporizers, and particularly for vaporizers for delivery of more volatile vaporizable materials, the inhalable dose may exist predominantly in the gas phase (i.e. formation of condensed phase particles may be very limited).

Vaporizers for use with liquid vaporizable materials (e.g., neat liquids, suspensions, solutions, mixtures, etc.) typically include an atomizer 141 in which a wicking element (also referred to herein as a wick (not shown in FIG. 1), which can include any material capable of causing fluid motion by capillary pressure) conveys an amount of a liquid vaporizable material to a part of the atomizer that includes a heating element (also not shown in FIG. 1). The wicking element is generally configured to draw liquid vaporizable material from a reservoir configured to contain (and that may in use contain) the liquid vaporizable material such that the liquid vaporizable material may be vaporized by heat delivered from a heating element. The wicking element may also optionally allow air to enter the reservoir to replace the volume of liquid removed. In other words, capillary action pulls liquid vaporizable material into the wick for vaporization by the heating element (described below), and air may, in some implementations of the current subject matter, return to the reservoir through the wick to at least partially equalize pressure in the reservoir. Other approaches to allowing air back into the reservoir to equalize pressure are also within the scope of the current subject matter.

The heating element can be or include one or more of a conductive heater, a radiative heater, and a convective heater. One type of heating element is a resistive heating element, which can be constructed of or at least include a material (e.g., a metal or alloy, for example a nickel-chromium alloy, or a non-metallic resistor) configured to dissipate electrical power in the form of heat when electrical current is passed through one or more resistive segments of the heating element. In some implementations of the current subject matter, an atomizer can include a heating element that includes resistive coil or other heating element wrapped around, positioned within, integrated into a bulk shape of, pressed into thermal contact with, or otherwise arranged to deliver heat to a wicking element to cause a liquid vaporizable material drawn by the wicking element from a reservoir to be vaporized for subsequent inhalation by a user in a gas and/or a condensed (e.g., aerosol particles or droplets) phase. Other wicking element, heating element, and/or atomizer assembly configurations are also possible, as discussed further below.

Certain vaporizers may also or alternatively be configured to create an inhalable dose of gas-phase and/or aerosol-phase vaporizable material via heating of a non-liquid vaporizable material, such as for example a solid-phase vaporizable material (e.g., a wax or the like) or plant material (e.g., tobacco leaves and/or parts of tobacco leaves) containing the vaporizable material. In such vaporizers, a resistive heating element may be part of or otherwise incorporated into or in thermal contact with the walls of an oven or other heating chamber into which the non-liquid vaporizable material is placed. Alternatively, a resistive heating element or elements may be used to heat air passing through or past the non-liquid vaporizable material to cause convective heating of the non-liquid vaporizable material. In still other examples, a resistive heating element or elements may be disposed in intimate contact with plant material such that direct conductive heating of the plant material occurs from within a mass of the plant material (e.g., as opposed to only by conduction inward form walls of an oven). Such non-liquid vaporizable materials may be used with cartridge using or cartridge less vaporizers.

The resistive heating element may be activated (e.g., a controller, which is optionally part of a vaporizer body as discussed below, may cause current to pass from the power source through a circuit including the resistive heating element, which is optionally part of a vaporizer cartridge as discussed below), in association with a user puffing (e.g., drawing, inhaling, etc.) on a mouthpiece 130 of the vaporizer to cause air to flow from an air inlet, along an airflow path that passes an atomizer (e.g., wicking element and heating element), optionally through one or more condensation areas or chambers, to an air outlet in the mouthpiece. Incoming air passing along the airflow path passes over, through, etc. the atomizer, where gas phase vaporizable material is entrained into the air. As noted above, the entrained gas-phase vaporizable material may condense as it passes through the remainder of the airflow path such that an inhalable dose of the vaporizable material in an aerosol form can be delivered from the air outlet (e.g., in a mouthpiece 130 for inhalation by a user).

Activation of the heating element may be caused by automatic detection of the puff based on one or more of signals generated by one or more sensors 113, such as for example a pressure sensor or sensors disposed to detect pressure along the airflow path relative to ambient pressure (or optionally to measure changes in absolute pressure), one or more motion sensors of the vaporizer, one or more flow sensors of the vaporizer, a capacitive lip sensor of the vaporizer; in response to detection of interaction of a user with one or more input devices 116 (e.g., buttons or other tactile control devices of the vaporizer 100), receipt of signals from a computing device in communication with the vaporizer; and/or via other approaches for determining that a puff is occurring or imminent.

As alluded to in the previous paragraph, a vaporizer consistent with implementations of the current subject matter may be configured to connect (e.g., wirelessly or via a wired connection) to a computing device (or optionally two or more devices) in communication with the vaporizer. To this end, the controller 104 may include communication hardware 105. The controller 104 may also include a memory 108. A computing device can be a component of a vaporizer system that also includes the vaporizer 100, and can include its own communication hardware, which can establish a wireless communication channel with the communication hardware 105 of the vaporizer 100. For example, a computing device used as part of a vaporizer system may include a general-purpose computing device (e.g., a smartphone, a tablet, a personal computer, some other portable device such as a smartwatch, or the like) that executes software to produce a user interface for enabling a user of the device to interact with a vaporizer. In other implementations of the current subject matter, such a device used as part of a vaporizer system can be a dedicated piece of hardware such as a remote control or other wireless or wired device having one or more physical or soft (e.g., configurable on a screen or other display device and selectable via user interaction with a touch-sensitive screen or some other input device like a mouse, pointer, trackball, cursor buttons, or the like) interface controls. The vaporizer can also include one or more output 117 features or devices for providing information to the user.

A computing device that is part of a vaporizer system as defined above can be used for any of one or more functions, such as controlling dosing (e.g., dose monitoring, dose setting, dose limiting, user tracking, etc.), controlling sessioning (e.g., session monitoring, session setting, session limiting, user tracking, etc.), controlling nicotine delivery (e.g., switching between nicotine and non-nicotine vaporizable material, adjusting an amount of nicotine delivered, etc.), obtaining locational information (e.g., location of other users, retailer/commercial venue locations, vaping locations, relative or absolute location of the vaporizer itself, etc.), vaporizer personalization (e.g., naming the vaporizer, locking/password protecting the vaporizer, adjusting one or more parental controls, associating the vaporizer with a user group, registering the vaporizer with a manufacturer or warranty maintenance organization, etc.), engaging in social activities (e.g., games, social media communications, interacting with one or more groups, etc.) with other users, or the like. The terms "sessioning", "session", "vaporizer session," or "vapor session," are used generically to refer to a period devoted to the use of the vaporizer. The period can include a time period, a number of doses, an amount of vaporizable material, and/or the like.

In the example in which a computing device provides signals related to activation of the resistive heating element, or in other examples of coupling of a computing device with a vaporizer for implementation of various control or other functions, the computing device executes one or more computer instructions sets to provide a user interface and underlying data handling. In one example, detection by the computing device of user interaction with one or more user interface elements can cause the computing device to signal the vaporizer 100 to activate the heating element, either to a full operating temperature for creation of an inhalable dose of vapor/aerosol. Other functions of the vaporizer may be controlled by interaction of a user with a user interface on a computing device in communication with the vaporizer.

The temperature of a resistive heating element of a vaporizer may depend on a number of factors, including an amount of electrical power delivered to the resistive heating element and/or a duty cycle at which the electrical power is delivered, conductive heat transfer to other parts of the electronic vaporizer and/or to the environment, latent heat losses due to vaporization of a vaporizable material from the wicking element and/or the atomizer as a whole, and convective heat losses due to airflow (e.g., air moving across the heating element or the atomizer as a whole when a user inhales on the electronic vaporizer). As noted above, to reliably activate the heating element or heat the heating element to a desired temperature, a vaporizer may, in some implementations of the current subject matter, make use of signals from a pressure sensor to determine when a user is inhaling. The pressure sensor can be positioned in the airflow path and/or can be connected (e.g., by a passageway or other path) to an airflow path connecting an inlet for air to enter the device and an outlet via which the user inhales the resulting vapor and/or aerosol such that the pressure sensor experiences pressure changes concurrently with air passing through the vaporizer device from the air inlet to the air outlet. In some implementations of the current subject matter, the heating element may be activated in association with a user's puff, for example by automatic detection of the puff, for example by the pressure sensor detecting a pressure change in the airflow path.

Typically, the pressure sensor (as well as any other sensors 113) can be positioned on or coupled (e.g., electrically or electronically connected, either physically or via a wireless connection) to the controller 104 (e.g., a printed circuit board assembly or other type of circuit board). To take measurements accurately and maintain durability of the vaporizer, it can be beneficial to provide a resilient seal 150 to separate an airflow path from other parts of the vaporizer. The seal 150, which can be a gasket, may be configured to at least partially surround the pressure sensor such that connections of the pressure sensor to internal circuitry of the vaporizer are separated from a part of the pressure sensor exposed to the airflow path. In an example of a cartridge-based vaporizer, the seal 150 may also separate parts of one or more electrical connections between a vaporizer body 110 and a vaporizer cartridge 120. Such arrangements of a seal 150 in a vaporizer 100 can be helpful in mitigating against potentially disruptive impacts on vaporizer components resulting from interactions with environmental factors such as water in the vapor or liquid phases, other fluids such as the vaporizable material, etc. and/or to reduce escape of air from the designed airflow path in the vaporizer. Unwanted air, liquid or other fluid passing and/or contacting circuitry of the vaporizer can cause various unwanted effects, such as alter pressure readings, and/or can result in the buildup of unwanted material, such as moisture, the vaporizable material, etc. in parts of the vaporizer where they may result in poor pressure signal, degradation of the pressure sensor or other components, and/or a shorter life of the vaporizer. Leaks in the seal 150 can also result in a user inhaling air that has passed over parts of the vaporizer device containing or constructed of materials that may not be desirable to be inhaled.

A general class of vaporizers that have recently gained popularity includes a vaporizer body 110 that includes a controller 104, a power source 112 (e.g., battery), one more sensors 113, charging contacts, a seal 150, and a cartridge receptacle 118 configured to receive a vaporizer cartridge 120 for coupling with the vaporizer body through one or more of a variety of attachment structures. In some examples, vaporizer cartridge 120 includes a reservoir 140 for containing a liquid vaporizable material and a mouthpiece 130 for delivering an inhalable dose to a user. The vaporizer cartridge can include an atomizer 141 having a wicking element and a heating element, or alternatively, one or both of the wicking element and the heating element can be part of the vaporizer body. In implementations in which any part of the atomizer 141 (e.g., heating element and/or wicking element) is part of the vaporizer body, the vaporizer can be configured to supply liquid vaporizer material from a reservoir in the vaporizer cartridge to the atomizer part(s) included in the vaporizer body.

In vaporizers in which the power source 112 is part of a vaporizer body 110 and a heating element is disposed in a vaporizer cartridge 120 configured to couple with the vaporizer body 110, the vaporizer 100 may include electrical connection features (e.g., means for completing a circuit) for completing a circuit that includes the controller 104 (e.g., a printed circuit board, a microcontroller, or the like), the power source, and the heating element. These features may include at least two contacts on a bottom surface of the vaporizer cartridge 120 (referred to herein as cartridge contacts 124) and at least two contacts disposed near a base of the cartridge receptacle (referred to herein as receptacle contacts 125) of the vaporizer 100 such that the cartridge contacts 124 and the receptacle contacts 125 make electrical connections when the vaporizer cartridge 120 is inserted into and coupled with the cartridge receptacle 118. The circuit completed by these electrical connections can allow delivery of electrical current to the resistive heating element and may further be used for additional functions, such as for example for measuring a resistance of the resistive heating element for use in determining and/or controlling a temperature of the resistive heating element based on a thermal coefficient of resistivity of the resistive heating element, for identifying a cartridge based on one or more electrical characteristics of a resistive heating element or the other circuitry of the vaporizer cartridge, etc.

In some examples of the current subject matter, the at least two cartridge contacts and the at least two receptacle contacts can be configured to electrically connect in either of at least two orientations. In other words, one or more circuits necessary for operation of the vaporizer can be completed by insertion of a vaporizer cartridge 120 in the cartridge receptacle 118 in a first rotational orientation (around an axis along which the end of the vaporizer cartridge having the cartridge is inserted into the cartridge receptacle 118 of the vaporizer body 110) such that a first cartridge contact of the at least two cartridge contacts 124 is electrically connected to a first receptacle contact of the at least two receptacle contacts 125 and a second cartridge contact of the at least two cartridge contacts 124 is electrically connected to a second receptacle contact of the at least two receptacle contacts 125. Furthermore, the one or more circuits necessary for operation of the vaporizer can be completed by insertion of a vaporizer cartridge 120 in the cartridge receptacle 118 in a second rotational orientation such that the first cartridge contact of the at least two cartridge contacts 124 is electrically connected to the second receptacle contact of the at least two receptacle contacts 125 and the second cartridge contact of the at least two cartridge contacts 124 is electrically connected to the first receptacle contact of the at least two receptacle contacts 125. This feature of a vaporizer cartridge 120 being reversibly insertable into a cartridge receptacle 118 of the vaporizer body 110 is described further below.

In one example of an attachment structure for coupling a vaporizer cartridge 120 to a vaporizer body, the vaporizer body 110 includes a detent (e.g., a dimple, protrusion, etc.) protruding inwardly from an inner surface the cartridge receptacle 118. One or more exterior surfaces of the vaporizer cartridge 120 can include corresponding recesses (not shown in FIG. 1) that can fit and/or otherwise snap over such detents when an end of the vaporizer cartridge 120 inserted into the cartridge receptacle 118 on the vaporizer body 110. When the vaporizer cartridge 120 and the vaporizer body 110 are coupled (e.g., by insertion of an end of the vaporizer cartridge 120 into the cartridge receptacle 118 of the vaporizer body 110, the detent into the vaporizer body 110 may fit within and/or otherwise be held within the recesses of the vaporizer cartridge 120 to hold the vaporizer cartridge 120 in place when assembled. Such a detent-recess assembly can provide enough support to hold the vaporizer cartridge 120 in place to ensure good contact between the at least two cartridge contacts 124 and the at least two receptacle contacts 125, while allowing release of the vaporizer cartridge 120 from the vaporizer body 110 when a user pulls with reasonable force on the vaporizer cartridge 120 to disengage the vaporizer cartridge 120 from the cartridge receptacle 118.

Further to the discussion above about the electrical connections between a vaporizer cartridge and a vaporizer body being reversible such that at least two rotational orientations of the vaporizer cartridge in the cartridge receptacle are possible, in some vaporizers the shape of the vaporizer cartridge, or at least a shape of the end of the vaporizer cartridge that is configured for insertion into the cartridge receptacle may have rotational symmetry of at least order two. In other words, the vaporizer cartridge or at least the insertable end of the vaporizer cartridge may be symmetric upon a rotation of 180° around an axis along which the vaporizer cartridge is inserted into the cartridge receptacle. In such a configuration, the circuitry of the vaporizer may support identical operation regardless of which symmetrical orientation of the vaporizer cartridge occurs.

In some examples, the vaporizer cartridge, or at least an end of the vaporizer cartridge configured for insertion in the cartridge receptacle may have a non-circular cross section transverse to the axis along which the vaporizer cartridge is inserted into the cartridge receptacle. For example, the non-circular cross section may be approximately rectangular, approximately elliptical (e.g., have an approximately oval shape), non-rectangular but with two sets of parallel or approximately parallel opposing sides (e.g., having a parallelogram-like shape), or other shapes having rotational symmetry of at least order two. In this context, approximately having a shape, indicates that a basic likeness to the described shape is apparent, but that sides of the shape in question need not be completely linear and vertices need not be completely sharp. Rounding of both or either of edges or vertices of the cross-sectional shape is contemplated in the description of any non-circular cross section referred to herein.

The at least two cartridge contacts and the at least two receptacle contacts can take various forms. For example, one or both sets of contacts may include conductive pins, tabs, posts, receiving holes for pins or posts, or the like. Some types of contacts may include springs or other urging features to cause better physical and electrical contact between the contacts on the vaporizer cartridge and the vaporizer body. The electrical contacts may optionally be gold-plated, and/or can include other materials.

Figure 2A:
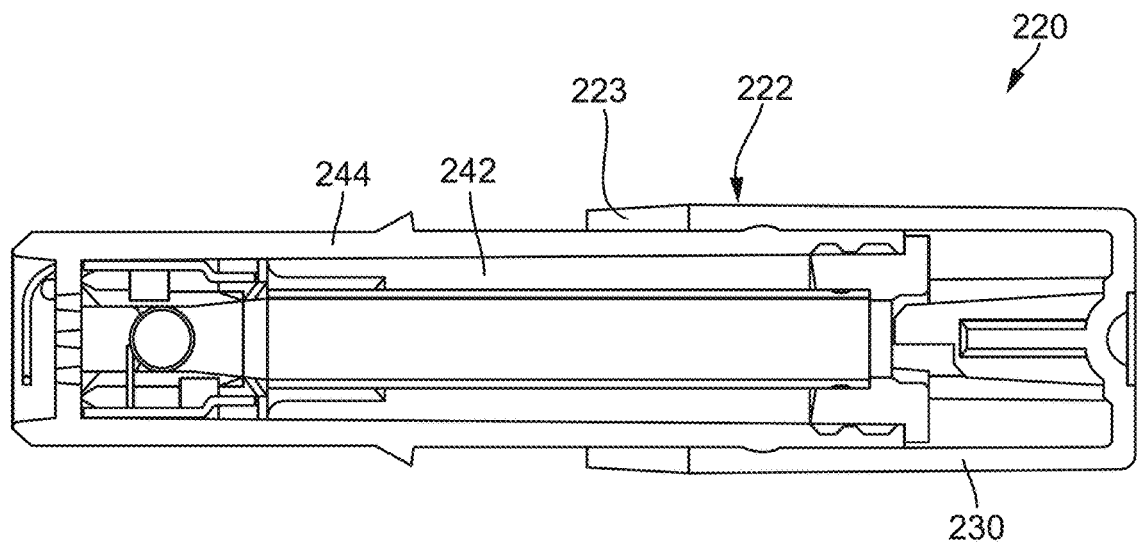
FIG. 2A illustrates a cross-sectional side view of a prior art vaporizer cartridge.
Figure 2B:
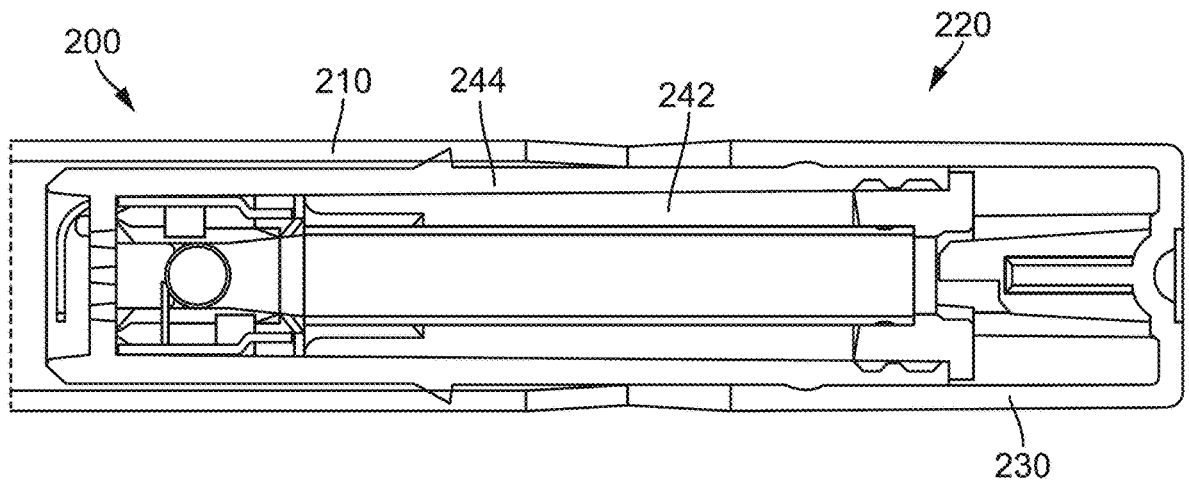
FIG. 2B illustrates a cross-sectional side view of a prior art vaporizer device including the vaporizer cartridge of FIG. 2A inserted in a vaporizer body.
Figure 2C:
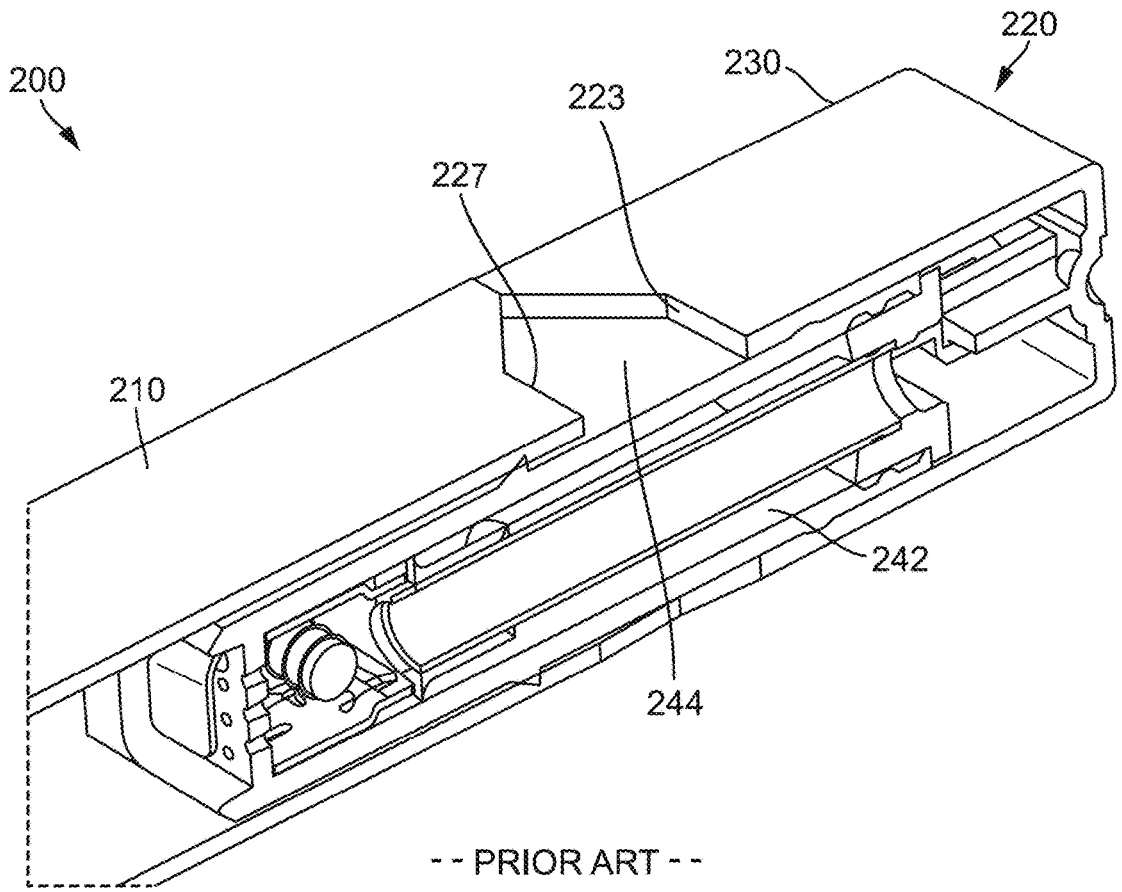
FIG. 2C illustrates a cross-sectional side view of the prior art vaporizer device of FIG. 2B.

As shown in example prior art FIGS. 2A-2C, some currently available vaporizer cartridges 220 are manufactured by coupling together a mouthpiece 230 and a reservoir housing 244 where an open end of the mouthpiece 230 slidably accepts an open end of the reservoir housing 244. As a result, a part of the open end of the mouthpiece 230 extends over a part of the open end of the reservoir housing 244 forming an overlapping section 222 of the vaporizer cartridge 220. For example, an approach for coupling the reservoir housing 244 to the mouthpiece 230 involves a snap-over coupling, press-fit coupling, welding, or the like. The overlapping section 222 can include a length of the vaporizer cartridge 220 that is double-walled (the wall of the mouthpiece 230 and the wall of the reservoir housing 244). As a result, the overlapping section 222 decreases or limits the volume of vaporizable material the cartridge can hold. To prolong the usable life of a single-use, prefilled cartridge and achieve desired effects from vaporizing the vaporizable material, maximizing the volume of the reservoir chamber (the chamber in the cartridge configured to contain the vaporizable material) without substantially increasing the overall size of the cartridge is desired and can maximize the value (e.g., more vaporizable material) provided to the consumer for each cartridge. Various cartridge embodiments described herein may maximize the reservoir chamber volume compared to the overall volume of the cartridge in a manner that may provide benefits relative to previously available approaches. Additionally, various cartridge embodiments and methods of assembling cartridges that improve cartridge cost, assembly efficiency, and/or prevention of tampering (e.g., unwanted refilling of cartridge). Other features and improvements upon the prior art are also described and within the scope of this disclosure.

Figure 3A:
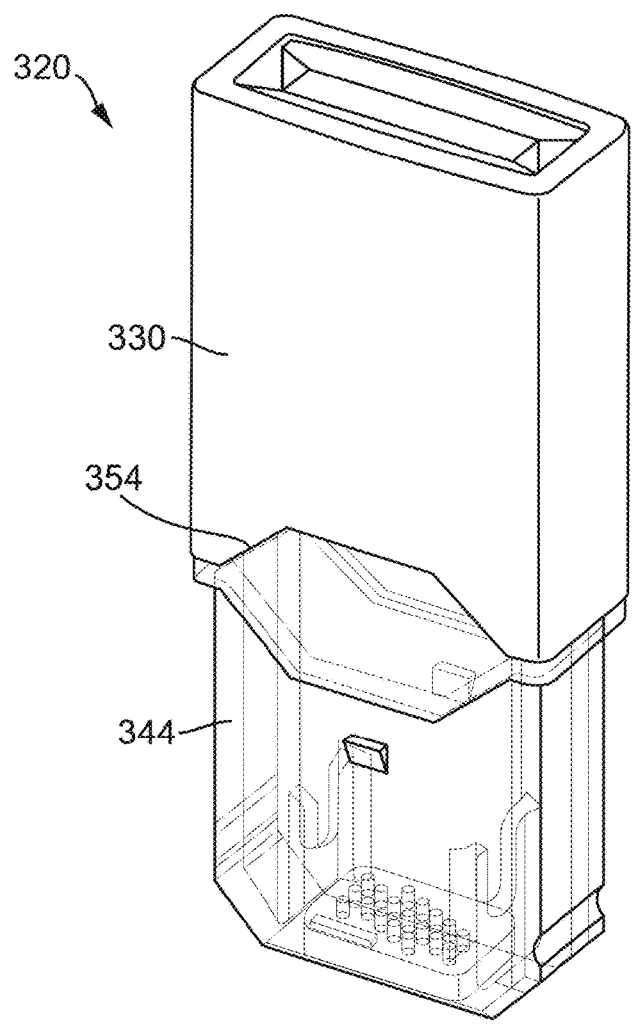
FIG. 3A illustrates a front perspective view of an embodiment of a vaporizer cartridge consistent with implementations of the current subject matter.
Figure 3B:
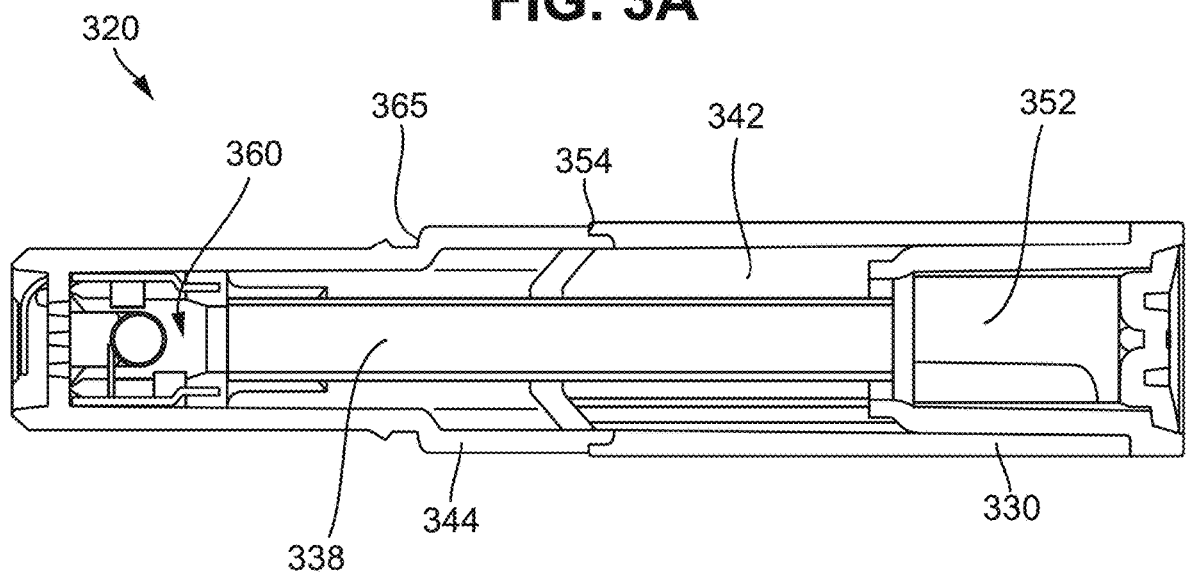
FIG. 3B illustrates a cross-sectional side view of the vaporizer cartridge of FIG. 3A.

FIGS. 3A-3B illustrate an embodiment of a vaporizer cartridge 320 consistent with implementations of the current subject matter. The vaporizer cartridge 320 includes a mouthpiece 330 coupled to a reservoir housing 344. As shown in FIG. 3B, the inner walls of the mouthpiece 330 are approximately co-planar with the inner walls of the reservoir housing 344 at least adjacent a first or coupling joint 354 between the mouthpiece 330 and the reservoir housing 344. Similarly, the outer walls of the mouthpiece 330 are approximately co-planar with the outer walls of the reservoir housing 344 at least adjacent the first joint 354 between the mouthpiece 330 and the reservoir housing 344. As such, the vaporizer cartridge 320 maintains an approximately uniform wall thickness along the length of the vaporizer cartridge 320 and thus maximizes an internal volume for containing a vaporizable material (e.g., the reservoir chamber 342 volume). The vaporizer cartridge 320 shown in FIG. 3A can thus have a larger vaporizable material containment volume (e.g., defined by the reservoir chamber 342) compared to the overall volume of the cartridge. In other words, the vaporizer cartridge 320 in FIG. 3A includes an embodiment of a maximized ratio of reservoir chamber 342 volume to overall cartridge volume. The vaporizer cartridge 320 can thus contain more vaporizable material for a given cartridge size while maintaining a desired compact configuration.

As shown in FIG. 3A, coupling of the mouthpiece to the reservoir does not result in the formation of a double-wall portion, such as the overlapping section 222 of the prior art vaporizer cartridge 220 shown in FIG. 2A. Instead, the presently described vaporizer cartridge 320 is able to maximize its reservoir chamber 342 volume by either molding or laser welding the mouthpiece 330 to the reservoir housing 344. This results in the formation of the first joint 354 that includes a chemical or material bond that secures the open end of the mouthpiece 330 to the open end of the reservoir housing 344. The chemical bond of the first joint 354 provides sufficient strength for maintaining the coupling of the reservoir housing 344 and mouthpiece 330, as well as provides sufficient sealing for preventing leakage of vaporizable material from the reservoir chamber 342. Further details regarding such methods of manufacturing are described in greater detail below.

For example, molding the mouthpiece 330 and the reservoir housing 344 together can include curing two different materials in a single mold, such as to achieve the reservoir housing 344 being transparent (e.g., to view the amount of vaporizable material contained therein) and the mouthpiece 330 being opaque (e.g., including a color to identify a type of vaporizable material). As such, a mold having a volume defining the vaporizer cartridge 320 can include two parts, such as a first part that defines the reservoir housing 344 and a second part that defines the mouthpiece 330. For example, during manufacturing, the first part can be filled with a translucent material and allowed to at least partly cure. The second part, which can be in fluid communication with the first part, can then be filled with a second, opaque material. After the first and second materials are cured, the volume of the mold can be released from the mold for final assembly, such as to include one or more parts (e.g., wick housing, airflow passageway, etc.) and/or vaporizable material. The first and second materials can include one or more of a variety of materials having one or more of a variety of different properties, such as being translucent, opaque, etc.

Some methods of manufacturing to achieve the improved vaporizer cartridge 320 configuration shown in FIG. 3A can include laser welding a molded mouthpiece 330 to a molded reservoir housing 344 to form the first joint 354. The coupling ends (e.g., the open ends of the mouthpiece 330 and reservoir housing 344) can include one or more of a variety of features for assisting with forming the first joint 354, including when formed under molding or laser welding methods of manufacturing. For example, the coupling ends forming a part of the first joint 354 can each include a complimenting step feature that allow some overlap between a part of a wall thickness of the mouthpiece 330 and a part of a wall thickness of the reservoir housing 344, such as shown in FIG. 3B. Other features along the coupling ends are within the scope of this disclosure.

Figure 3C:
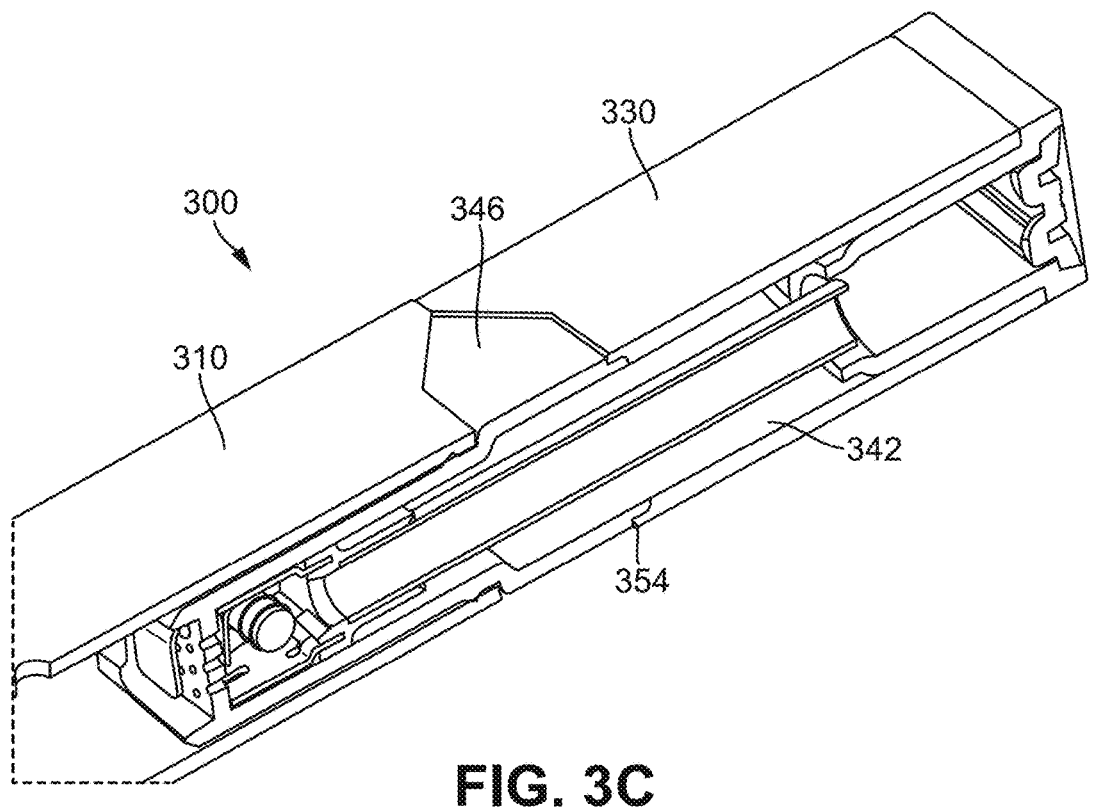
FIG. 3C illustrates a cross-sectional perspective view of a vaporizer device including the vaporizer cartridge of FIG. 3A inserted in a vaporizer body.
Figure 3D:
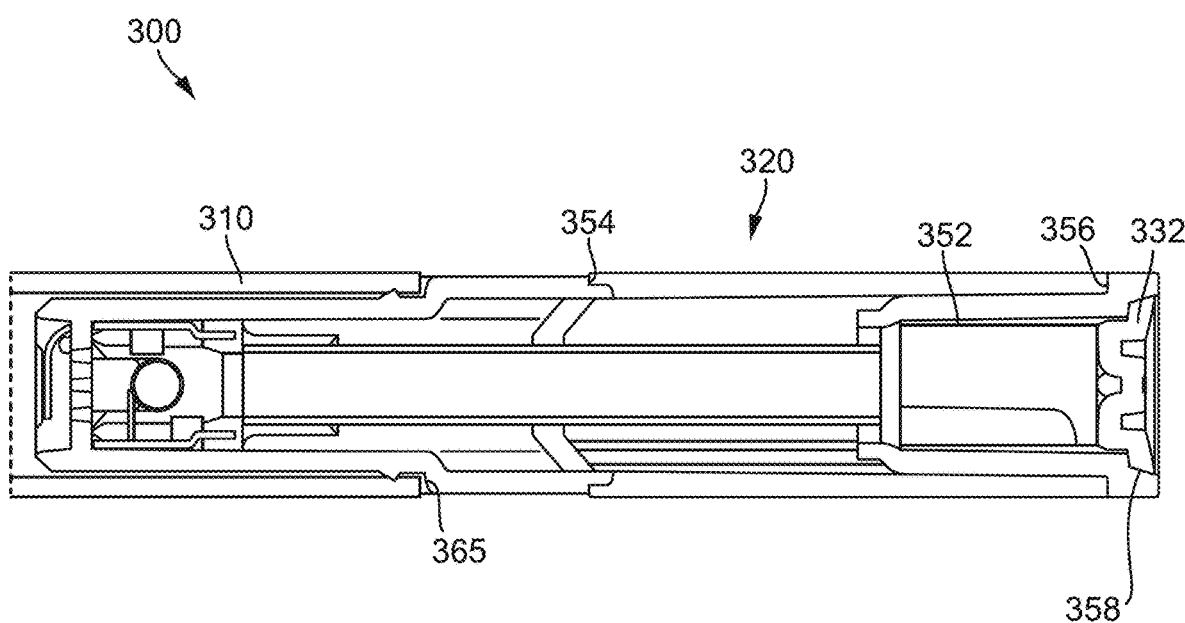
FIG. 3D illustrates a cross-sectional side view of the vaporizer device of FIG. 3C.

FIGS. 3C and 3D show a vaporizer device 300 including a vaporizer body 310 with the vaporizer cartridge 320 inserted into an insertion end of the vaporizer body 310. In such a configuration, the vaporizer device 300 can be used by a user to vaporize vaporizable material and inhale aerosol formed in the vaporizer device 300. The vaporizer cartridge 320 can include various features for assisting with either aligning or coupling the vaporizer cartridge 320 to the vaporizer body 310. For example, the reservoir housing 344 can include a notch or step 365 along one or more sides of the reservoir housing 344, as shown in FIGS. 3A and 3B. The notch 365 can provide a number of benefits, including providing a stop for preventing over-insertion of the vaporizer cartridge 320 into the insertion end of the vaporizer body 310, as well as increase the cross-section of the reservoir chamber 342 to thereby allow more vaporizable material to be contained within the vaporizer cartridge 320.

As shown in FIG. 3D, the notch 365 can be sized and shaped to allow a distal end of the insertion end of the vaporizer body 310 to mate against the notch 365, thereby providing a secure stop for preventing over insertion of the vaporizer cartridge 320 into the insertion end of the vaporizer body 310.

As shown in FIG. 3C, a window 346 can be displayed when the vaporizer cartridge 320 is coupled to the vaporizer body 310, which allows a user to view the contents of the vaporizer cartridge 320 when the vaporizer cartridge 320 is coupled to the vaporizer body 310. The window 346 can be part of the reservoir housing 344 that is made out of a translucent material. Other features, such as molded or laser-welded features, can be included in the vaporizer cartridge 320 that are within the scope of this disclosure.

Other components of the vaporizer cartridge 320 can be included and assembled to the vaporizer cartridge 320, including a tubing for forming a part of the airflow passageway, a wick housing for housing the wick and vaporization chamber, and a filter housing for housing at least one filter within the mouthpiece. For example, the filter housing can include a bucket shape that allows at least one filter to be placed within the bucket-shaped filter housing. The filter housing can include a passageway to allow the airflow passageway to couple thereto, thereby allowing airflow (e.g., aerosol) traveling through the cartridge to be placed in contact with the at least one filter before being inhaled by the user. In some embodiments, the filters are positioned off-axis or away from the airflow passageway such that airflow is not passed directly through the filters and, instead, is passed along a surface of one or more filters. In some embodiments, a filter may occupy most of the bucket of the filter housing and include a through-hole that aligns with the airflow passageway thereby allowing airflow to pass through and along the surface of the through-hole in the filter. Various embodiments of the filter and filter housing are within the scope of this disclosure. Assembly of such features (e.g., filter housing, airflow passageway, wick housing, etc.) can be time consuming and may require sealing to prevent fluid (e.g., air, aerosol, vaporization fluid) from leaking between parts. As such, combining more than one component together in a single part may result in more time and cost efficient assembly of the cartridge.

Figure 4:
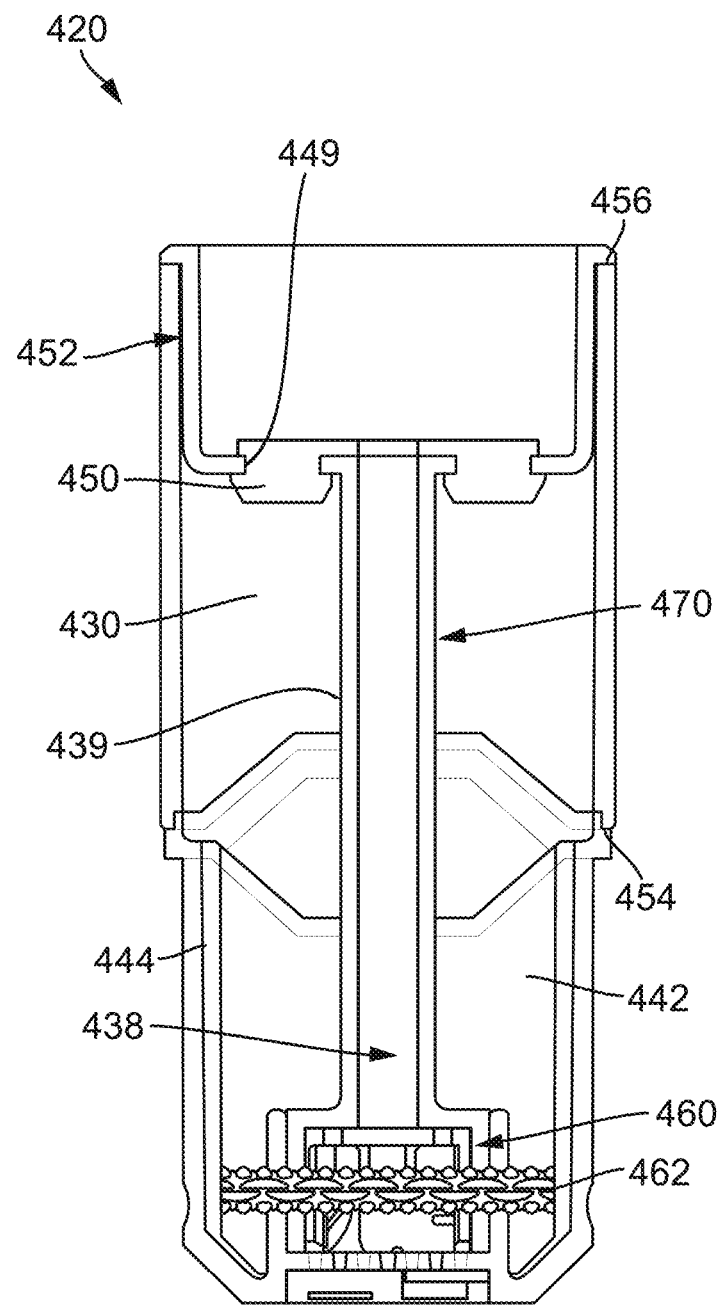
FIG. 4 illustrates a cross-sectional front view of another embodiment of a vaporizer cartridge including a molded air tube assembly.

FIG. 4 illustrates a cross-sectional front view of another embodiment of a vaporizer cartridge 420 having a mouthpiece 430 coupled to a reservoir housing 444 along a first joint 454, such as described above. Additionally, the vaporizer cartridge 420 includes a molded air tube assembly 470 that can include a single part that replaces more than two, such as three or more, distinct parts of some previously available cartridges. For example, the air tube assembly 470 can include a wick housing portion 460, a tubing portion 439 forming a part of the airflow passageway 438, and a filter housing portion 452. The wick housing portion 460 can include features and functions similar to a wick housing (such as the wick housing 360 in FIG. 3B), which is configured to contain a wick 462 and heating element in a vaporization chamber for forming aerosol to be inhaled by a user. Additionally, the filter housing portion 452 can include features and functions similar to a filter housing (such as the filter housing 352 in FIG. 3B), which is configured to contain at least one filter for filtering the aerosol formed in the vaporization device prior to being inhaled by a user. The tubing portion 439 can include features and functions similar to the tubing forming a part of the airflow passageway (such as the tubing 338 in FIG. 3B) and provides fluid communication between the filter housing (such as the filter housing 352 in FIG. 3B) and the wick housing (such as the wick housing 360 in FIG. 3B). To prevent leaking between the coupling joints, such as between the tubing and filter housing, as well as between the tubing and wick housing, a seal or sealing feature may be required, which can add cost and complexity to the cartridge assembly. In contrast, the air tube assembly 470 does not require the addition of a seal or sealing feature between the tubing portion 439 and the wick housing portion 460 or between the tubing portion 439 and the filter housing portion 452. This is because the air tube assembly 470 is a single part, such as molded into a single part, and thus does not include any coupling joints along the air tube assembly 470 that may allow fluid to leak therethrough. As such, the air tube assembly 470 can result in improved functioning as the reliance on proper functioning of one or more seals are removed from the cartridge.

Other configurations of the air tube assembly 470 are within the scope of this disclosure. For example, some embodiments of the air tube assembly 470 can include at least one port 449 that allows a seal or septum 450 to be coupled therein for providing a fluidic seal and thereby preventing vaporizable material from freely flowing through the at least one port 449. The port 449 can provide a passageway for filling the reservoir chamber 442 with vaporizable material, such as after the tubing assembly is coupled to either the mouthpiece or reservoir housing. For example, the tubing assembly can be coupled to the reservoir housing along a second joint 456, such as by laser welding a part of the air tube assembly 470 (e.g., the filter housing portion 452) to a part of the reservoir housing 444 to form a chemical or material bond along the second joint 456. The at least one port 449 can allow the filling, and refiling, of the reservoir chamber 442 with vaporizable material, such as by removing the seal 450 or piercing the seal 450 with a lumen for delivering the vaporizable material therethrough. In some instances, it may be desired to prevent the ability of the reservoir chamber 442 to be refilled. The following discusses another embodiment of the air tube assembly 470 that can assist with preventing refilling of the vaporizer cartridge 420, as well as provide a further increase in reservoir chamber volume ratio to overall cartridge volume.

For example, the air tube assembly 470 can include a metal tubing portion 439 that is coupled to the filter housing portion 452 and wick housing portion 460. During assembly, the air tube assembly 470 can be coupled to at least the mouthpiece 430 or reservoir housing 444. For example, the filter housing portion 452 of the air tube assembly 470 can be coupled to the reservoir housing 444 along the second joint 456, such as by laser welding to form a chemical or material bond along the second joint 456. In such a configuration, the filter housing portion 452 does not include a port and instead provides a barrier and fluidic seal that contains the vaporizable material in the reservoir chamber 442, as well as prevents re-filling of the vaporizer cartridge 420. As such, the vaporizable material is added to the reservoir chamber 442 prior to coupling the air tube assembly 470 to at least one of the mouthpiece 430 or reservoir housing 444. The prevention of re-filling the reservoir chamber 442 can assist with preventing tampering or improper usage of the vaporizer cartridge 420. Additionally, the metal tubing portion can include thinner walls compared to the molded tubing portion embodiment to thereby achieve the desired and/or appropriate structural strength and integrity of the tubing portion 439. As a result of the thinner walls, more volume of the reservoir chamber 442 can be achieved without having to increase the overall dimensions of the vaporizer cartridge 420, thereby further increasing the reservoir chamber volume percentage.

In some embodiments, a cap (such as the cap 332 show in FIG. 3D) can be coupled to an open end of the filter housing or filter housing portion to secure a filter in the filter housing or filter housing portion. For example, the cap 332 can be laser welded along a third joint 358, as shown in FIG. 3D. Similarly, the cap can be laser welded to the filter housing portion 452 of the vaporizer cartridge 420 illustrated in FIG. 4.

Exemplary Nicotine Liquid Formulations

Included herein are, inter alia, nicotine liquid formulations for use in electronic nicotine delivery systems (ENDS), such as devices provided herein. In embodiments, a nicotine liquid formulation includes nicotine and an acid such as an organic acid. In embodiments, a nicotine liquid formulation includes a liquid carrier.

Nicotine is a chemical stimulant and increases, for example, heart rate and blood pressure when provided to an animal, e.g., a mammal such as a human. The stimulant effect of nicotine may be referred to herein as nicotine stimulant effect. In embodiments, the stimulant effect is correlated to the nicotine serum level. In embodiments, nicotine transfer to a subject is associated with a feeling of physical and/or emotional satisfaction. In embodiments, the devices and formulations provided herein are useful for reducing a user's craving for a traditional cigarette.

Aspects of the present disclosure relate to formulations and devices for eliciting a nicotine-related biological effect (e.g., a nicotine stimulant effect) in a user. In embodiments, the nicotine-related biological effect (e.g., a nicotine stimulant effect) is comparable to that of a traditional cigarette such as a Pall Mall® or Newport 100® cigarette. In embodiments the traditional cigarette is the type of cigarette preferred by the user. A "nicotine-related biological effect" is an effect that is detectable by the user (e.g., subject) and includes, but is not limited to, a stimulating effect (also referred to herein as a nicotine stimulant effect) or a relaxing effect (e.g., reduced anxiety or irritability). In embodiments, the nicotine-related biological effect is a stimulating effect (also referred to herein as a nicotine stimulant effect). In embodiments, a nicotine-related biological effect is improved concentration. In embodiments, a nicotine-related biological effect is increased alertness. A nicotine stimulant effect may manifest as, for example, an increase in heart rate, an increase in blood pressure, and/or a feeling of satisfaction (e.g., physical satisfaction or emotional satisfaction) of a user. In embodiments, an increased nicotine-related biological effect (e.g., a nicotine stimulation effect, such as a faster rise in heart rate) may be achieved, for example, within about 10 seconds, about 20 seconds, about 40 seconds, about 60 seconds, about 80 seconds, about 100 seconds, about 120 seconds, about 140 seconds, about 160 seconds, about 180 seconds, about 200 seconds, about 220 seconds, about 240 seconds, about 260 seconds, about 280 seconds, about 300 seconds, about 320 seconds, about 340 seconds, about 360 seconds, about 7 minutes, about 8 minutes, about 9 minutes or about 10 minutes following delivery of nicotine or protonated nicotine in accordance with the teachings of the present disclosure. In embodiments, the nicotine stimulant effect is an increase in heart rate. The increase in heart rate may be achieved, for example, within about 10 seconds, about 20 seconds, about 40 seconds, about 60 seconds, about 80 seconds, about 100 seconds, about 120 seconds, about 140 seconds, about 160 seconds, about 180 seconds, about 200 seconds, about 220 seconds, about 240 seconds, about 260 seconds, about 280 seconds, about 300 seconds, about 320 seconds, about 340 seconds, about 360 seconds, about 7 minutes, about 8 minutes, about 9 minutes or about 10 minutes following delivery of nicotine or protonated nicotine in accordance with the teachings of the present disclosure. In embodiments, the effective amount of nicotine (e.g., protonated nicotine) raises the heart rate of a user by about 10%, or about 15%, or about 20%, or about 25%, or about 30%, or about 35%, or about 40%, or about 45%, or about 50%, or about 55%, or about 60% relative to the heart rate of the user prior to the delivery of nicotine (e.g., protonated nicotine) in accordance with the teachings of the present disclosure. In embodiments, the effective amount of protonated nicotine raises the heart rate of a user by about 10%, or about 15%, or about 20%, or about 25%, or about 30%, or about 35%, or about 40%, or about 45%, or about 50%, or about 55%, or about 60% relative to the heart rate of a corresponding user who receives an the same amount of nicotine in free base form. In embodiments, the heart rate is resting heart rate. In embodiments, the nicotine-related biological effect is reduced craving for a cigarette. In embodiments, the reduced craving is experienced within about 10 seconds, about 20 seconds, about 40 seconds, about 60 seconds, about 80 seconds, about 100 seconds, about 120 seconds, about 140 seconds, about 160 seconds, about 180 seconds, about 200 seconds, about 220 seconds, about 240 seconds, about 260 seconds, about 280 seconds, about 300 seconds, about 320 seconds, about 340 seconds, about 360 seconds, about 7 minutes, about 8 minutes, about 9 minutes or about 10 minutes following delivery of nicotine or protonated nicotine in accordance with the teachings of the present disclosure. In embodiments, the nicotine-related biological effect is an enjoyable sensation in the throat or chest. In embodiments, the nicotine-related biological effect is any combination of 2, 3, 4, 5, or more effects associated with nicotine disclosed herein or known in the art. Such effects are not limited to what a user can perceive, and thus can include both objective and subjective effects.

In embodiments, use of a nicotine liquid formulation provided herein mimics the peak nicotine delivery of a traditional cigarette. In embodiments, the $C_{max}$ and/or $T_{max}$ value(s) for a user's plasma nicotine levels are comparable to those of a traditional cigarette (or are approaching that of a traditional cigarette, e.g., are 90-100% or at least about 80%, 85%, 90%, or 95% the $C_{max}$ and/or $T_{max}$ value of the traditional cigarette). In embodiments, the rate of nicotine uptake in the plasma of blood of users is about the same as that of a traditional cigarette (e.g., the $C_{max}$ and $T_{max}$ values are at least about 90% of the $C_{max}$ and $T_{max}$ values of a traditional cigarette). In embodiments, the rate of nicotine uptake in the plasma or blood of users is less than that of the traditional cigarette, but sufficient to, e.g., reduce craving for the traditional cigarette. In embodiments, formulations (e.g., nicotine-organic acid formulations) that demonstrate the quickest rate of nicotine uptake in the plasma are more preferred in satisfaction evaluations, and are rated more equivalent to cigarette satisfaction than the formulations showing the slower rates of rise of nicotine in plasma. In embodiments, a user rates his or her satisfaction level as at least a 3 on a scale ranging from 1 to 7, where 1=not at all, 2=very little, 3=a little, 4=moderately, 5=a lot, 6=quite a lot and 7=extremely. In embodiments, the user rates his or her satisfaction level a 4 on the scale. In embodiments, the user rates his or her satisfaction level a 5 on the scale. In embodiments, the user rates his or her satisfaction level as a 6 on the scale. In embodiments, the user rates his or her satisfaction level a 7 on the scale.

In an aspect, a nicotine liquid formulation is provided including nicotine, an acid (such as an organic acid), and a liquid carrier. In embodiments, when heating the formulation, an inhalable aerosol is formed comprising an effective amount of nicotine and/or protonated nicotine. In embodiments, when heating the formulation, an inhalable aerosol is formed comprising an effective amount of protonated nicotine. In embodiments, the formulation is in a cartridge. In embodiments, the cartridge is in an electronic nicotine delivery system. An "effective amount" of a compound (such as nicotine) is an amount sufficient for the compound to accomplish a stated purpose relative to the absence of the compound (e.g., achieve the effect for which it is administered). The term "effective amount" also includes an amount that is more sufficient to accomplish the stated purpose, provided the stated purpose is accomplished without undue adverse side effects (such as toxicity or irritation) commensurate with a reasonable benefit/risk ratio when used in the manner of this disclosure. In embodiments, an effective amount of nicotine (such as protonated nicotine, free base nicotine, or a combination thereof) is an amount of nicotine that is sufficient to result in a nicotine-related biological effect (e.g., a nicotine stimulant effect) in a user.

In an aspect, a method of providing nicotine to a user (also referred to herein as a subject) of an electronic nicotine delivery system is provided. "Providing" nicotine to a user includes making nicotine available (such as via an electronic nicotine delivery system) or administering nicotine (such as via an electronic nicotine delivery system) to a user. In embodiments, the administration is self-administration. In embodiments, "providing" nicotine to a user may include making available to, selling to, and/or delivering to a user who wishes to self-administer nicotine a device that is configured to be operated by the user. In embodiments, nicotine is self-administered by inhaling aerosol comprising the nicotine, wherein the nicotine is produced by the device when the device is operated.

In embodiments, the method includes (a) heating a nicotine liquid formulation in an electronic nicotine delivery system to produce an inhalable aerosol, wherein the formulation includes nicotine and organic acid in a liquid carrier; and (b) inhalation of the aerosol by the user, wherein the aerosol includes protonated nicotine in an amount such that the user experiences a nicotine-related biological effect.

In embodiments, the method includes (a) heating a nicotine liquid formulation in an electronic nicotine delivery system to produce an inhalable aerosol, wherein the formulation includes nicotine and organic acid in a liquid carrier; and (b) inhalation of the aerosol by the user, wherein the aerosol includes the organic acid in an amount such that the user experiences a nicotine-related biological effect.

In embodiments, the method includes (a) heating a nicotine liquid formulation in an electronic nicotine delivery system to produce an inhalable aerosol, wherein the formulation includes nicotine and organic acid in a liquid carrier; and (b) inhalation of the aerosol by the user, wherein the aerosol includes nicotine and an amount of organic acid sufficient to, subsequent to inhalation by a user, cause an increased nicotine-related biological effect in the user relative to the absence of the organic acid.

In embodiments, the method includes (a) (the user) operating an electronic nicotine delivery system as disclosed herein including a nicotine liquid formulation, the formulation including nicotine, an organic acid, and a liquid carrier, wherein the electronic nicotine delivery system heats the formulation to an operating temperature, such that an inhalable aerosol including an effective amount of protonated nicotine is produced; and (b) (the user) inhaling the inhalable aerosol. Operating an electronic nicotine delivery system includes activating the essential electronic components of the electronic nicotine delivery system to allow for the heating and inhalation. In embodiments, operating an electronic nicotine delivery system comprises, consists essentially of, or consists of the user holding the electronic nicotine delivery system and drawing from on a mouthpiece of the electronic nicotine delivery system. In embodiments, the effective amount is an amount such that the user experiences a nicotine-related biological effect upon inhalation.

In embodiments, an effective amount of nicotine is effective to reduce a user's craving for a traditional cigarette. In embodiments, the craving is completely reduced such that the user has no craving for the traditional cigarette. In embodiments, the nicotine-related biological effect is a physiological response that is similar or equivalent to the response from nicotine provided by smoking traditional cigarette. In embodiments, the nicotine-related biological effect is nicotine stimulation that mimics (e.g., is equivalent to) that of a traditional cigarette. In embodiments, the nicotine-related biological effect is increased heart rate that mimics the increased heart rate of a user who is smoking a traditional cigarette. The heart rate of a user who is smoking a traditional cigarette may be referred to herein as the "heart rate of a traditional cigarette." An increased heart rate "mimics" that of a traditional cigarette if the heart rate is about the same as, has about the same magnitude as, or has the about same rate of increase compared to the heart rate of a traditional cigarette.

In embodiments, the method includes (a) heating a nicotine liquid formulation in an electronic nicotine delivery system to produce an inhalable aerosol, wherein the formulation includes nicotine and organic acid in a liquid carrier; and (b) inhalation of the aerosol by the user, wherein the organic acid is present in an amount such that the user has reduced or no craving for a traditional cigarette.

In embodiments, the method includes (a) heating a nicotine liquid formulation in an electronic nicotine delivery system to produce an inhalable aerosol, wherein the formulation includes nicotine and organic acid in a liquid carrier; and (b) inhalation of the aerosol by the user, wherein the organic acid is present in an amount such that the user has a physiological response that is similar or equivalent to the response from nicotine provided by smoking traditional cigarette.

In embodiments, the method includes (a) heating a nicotine liquid formulation in an electronic nicotine delivery system to produce an inhalable aerosol, wherein the formulation includes nicotine and organic acid in a liquid carrier; and (b) inhalation of the aerosol by the user, wherein the organic acid is present in an amount such that the user experiences increased nicotine-related biological effect (e.g., a faster rise in heart rate) that mimics that of a traditional cigarette.

In embodiments, the method includes (a) heating a nicotine liquid formulation in an electronic nicotine delivery system to produce an inhalable aerosol, wherein the formulation includes nicotine and an organic acid in a liquid carrier; and (b) inhalation of the aerosol by the user, wherein the organic acid is present in an amount sufficient to provide nicotine stimulation that mimics that of a traditional cigarette.

In embodiments, the aerosol includes protonated nicotine sufficient to, subsequent to inhalation by a user, cause a rise in the level of plasma nicotine in the user that mimics a traditional cigarette.

In embodiments, the method includes (a) heating a nicotine liquid formulation in an electronic nicotine delivery system to produce an inhalable aerosol, wherein the formulation includes nicotine and benzoic acid in a liquid carrier, wherein the formulation includes an amount of protonated nicotine of about 0.5% to about 5% or about 1.5% to about 2.5%; and (b) inhalation of the aerosol by the user. In embodiments, most or all of the nicotine is protonated in the formulation. In embodiments, at least 85-95%, 85-90%, 85-99%, 90-95%, 90-99%, or 95-99% of the nicotine in the formulation is protonated. In embodiments, at least about 85%, 86%, 87%, 88%, 89%, 90%, 91%, 92%, 93%, 94%, 95%, 96%, 97%, 98%, or 99% of the nicotine is protonated. In embodiments, from about 85%, 86%, 87%, 88%, 89%, or 90% to about 91%, 92%, 93%, 94%, 95%, 96%, 97%, 98%, or 99% of the nicotine is protonated. In embodiments, 100% of the nicotine is protonated. In embodiments, at least 85% of the nicotine is protonated. In embodiments, at least 90% of the nicotine is protonated. In embodiments, at least 91% of the nicotine is protonated. In embodiments, at least 92% of the nicotine is protonated. In embodiments, at least 93% of the nicotine is protonated. In embodiments, at least 94% of the nicotine is protonated. In embodiments, at least 95% of the nicotine is protonated. In embodiments, at least 96% of the nicotine is protonated. In embodiments, at least 97% of the nicotine is protonated. In embodiments, at least 98% of the nicotine is protonated. In embodiments, at least 99% of the nicotine is protonated.

In embodiments, more or all of the nicotine in an aerosol produced (e.g., in a device, or according to a method provided herein) is protonated. In embodiments, at least 85-95%, 85-90%, 85-99%, 90-95%, 90-99%, or 95-99% of the nicotine in the aerosol is protonated. In embodiments, at least about 85%, 86%, 87%, 88%, 89%, 90%, 91%, 92%, 93%, 94%, 95%, 96%, 97%, 98%, or 99% of the nicotine is protonated. In embodiments, from about 85%, 86%, 87%, 88%, 89%, or 90% to about 91%, 92%, 93%, 94%, 95%, 96%, 97%, 98%, or 99% of the nicotine is protonated. In embodiments, 100% of the nicotine is protonated. In embodiments, at least 85% of the nicotine is protonated. In embodiments, at least 90% of the nicotine is protonated. In embodiments, at least 91% of the nicotine is protonated. In embodiments, at least 92% of the nicotine is protonated. In embodiments, at least 93% of the nicotine is protonated. In embodiments, at least 94% of the nicotine is protonated. In embodiments, at least 95% of the nicotine is protonated. In embodiments, at least 96% of the nicotine is protonated. In embodiments, at least 97% of the nicotine is protonated. In embodiments, at least 98% of the nicotine is protonated. In embodiments, at least 99% of the nicotine is protonated.

In embodiments, the method includes (a) heating a nicotine liquid formulation in an electronic nicotine delivery system to produce an inhalable aerosol, wherein the formulation includes nicotine and benzoic acid in a liquid carrier; and (b) inhalation of the aerosol by the user.

In embodiments, the method includes (a) heating a nicotine liquid formulation in an electronic nicotine delivery system to produce an inhalable aerosol, wherein the formulation includes nicotine and lactic acid in a liquid carrier; and (b) inhalation of the aerosol by the user.

In embodiments, the method includes (a) heating a nicotine liquid formulation in an electronic nicotine delivery system to produce an inhalable aerosol, wherein the formulation includes nicotine, benzoic acid, and lactic acid in a liquid carrier; and (b) inhalation of the aerosol by the user.

In an aspect, a method of producing an inhalable aerosol comprising nicotine and benzoic acid is provided. In embodiments, the method includes heating nicotine and benzoic acid in an electronic inhaler to produce the aerosol, wherein the aerosol includes nicotine and an amount of benzoic acid sufficient to, subsequent to inhalation by a user, cause an increased nicotine-related biological effect (e.g., a faster rise in heart rate) in the user relative to the absence of the benzoic acid. In an aspect, a method of producing an inhalable aerosol comprising nicotine and lactic acid is provided. In embodiments, the method includes heating nicotine and lactic acid in an electronic inhaler to produce the aerosol, wherein the aerosol includes nicotine and an amount of lactic acid sufficient to, subsequent to inhalation by a user, cause an increased nicotine-related biological effect (e.g., a faster rise in heart rate) relative to the absence of the lactic acid. In an aspect, a method of producing an inhalable aerosol comprising nicotine, benzoic acid, and lactic acid is provided. In embodiments, the method includes heating nicotine and benzoic acid and lactic acid in an electronic inhaler to produce the aerosol, wherein the aerosol includes nicotine and an amount of benzoic acid and lactic acid sufficient to, subsequent to inhalation by a user, cause an increased nicotine-related biological effect (e.g., a faster rise in heart rate) in the user relative to the absence of the benzoic acid and the lactic acid.

In embodiments, the method includes heating a nicotine liquid formulation in an electronic nicotine delivery system to produce an inhalable aerosol, the formulation comprising nicotine and one or more organic acids in a liquid carrier, wherein the one or more organic acids include a keto acid, an aliphatic monocarboxylic acid, an aliphatic dicarboxylic acid, an aromatic acid, and/or a hydroxyacid.

In embodiments, the method includes heating a nicotine liquid formulation in an electronic nicotine delivery system to produce an inhalable aerosol, the formulation comprising nicotine and a carboxylic acid in a liquid carrier, wherein the carboxylic acid is a beta-keto acid, an aliphatic monocarboxylic acid, an aromatic acid, or a hydroxyacid. In embodiments, the formulation includes an amount of the carboxylic acid sufficient to, subsequent to inhalation, cause an increased nicotine-related biological effect (e.g., a faster rise in heart rate) in the user relative to the absence of the carboxylic acid. In embodiments, the formulation includes an amount of the carboxylic acid sufficient to, subsequent to inhalation, cause a faster rise in heart rate in the user relative to the absence of the carboxylic acid.

In embodiments, the method includes heating a nicotine liquid formulation in an electronic nicotine delivery system to produce an inhalable aerosol, the formulation comprising nicotine and an organic acid in a liquid carrier, wherein (a) the formulation includes an amount of the organic acid sufficient to, subsequent to inhalation, cause an increased nicotine-related biological effect (e.g., a faster rise in heart rate) in the user relative to the absence of the organic acid; and (b) the electronic nicotine delivery system includes a cartridge, wherein the cartridge serves as a reservoir that holds the formulation and as a mouthpiece for the electronic nicotine delivery system.

In embodiments, the method includes heating a nicotine liquid formulation in an electronic nicotine delivery system to produce an inhalable aerosol, the formulation comprising nicotine and an organic acid in a liquid carrier, wherein (a) the pH of the liquid formulation is sufficiently acidic to, subsequent to inhalation, cause an increased nicotine-related biological effect (e.g., a faster rise in heart rate) in the user relative to the absence of the organic acid; and (b) the electronic nicotine delivery system includes a cartridge, wherein the cartridge serves as a reservoir that holds the formulation and as a mouthpiece for the electronic nicotine delivery system. In embodiments, the pH of the formulation is less than 7.0. In embodiments, the pH of the formulation is from about 2.5 to about 6.5. In embodiments, the pH of the formulation is from about 3 to about 6.5. In embodiments, the pH of the formulation is from about 4 to about 6.5. In embodiments, the pH of the formulation is from about 5 to about 6.5. In embodiments, the pH of the formulation is from about 6 to about 6.5. In embodiments, the pH of the formulation is from about 3 to about 5.5. In embodiments, the pH of the formulation is from about 3.5 to about 5.5. In embodiments, the pH of the formulation is about 2.5, 3, 3.5, 4, 4.5, 5, 5.5, 6, or 6.5.

In embodiments, the aerosol includes level of protonated nicotine such that the user has about 80-100% or at least about 80%, 85%, 86%, 87%, 88%, 89%, 90%, 91%, 92%, 93%, 94%, 95%, 96%, 97%, 98%, or 99% the plasma nicotine $C_{max}$ value of a traditional cigarette. In embodiments, the aerosol includes level of protonated nicotine such that the user has about 80-100% or at least about 80%, 85%, 86%, 87%, 88%, 89%, 90%, 91%, 92%, 93%, 94%, 95%, 96%, 97%, 98%, or 99% the plasma nicotine $T_{max}$ value of a traditional cigarette.

In embodiments, the aerosol includes an amount of nicotine in combination with organic acid such that the user has about 80-100% or at least about 80%, 85%, 86%, 87%, 88%, 89%, 90%, 91%, 92%, 93%, 94%, 95%, 96%, 97%, 98%, or 99% the plasma nicotine $C_{max}$ value of a traditional cigarette. In embodiments, the aerosol includes an amount of nicotine in combination with organic acid such that the user has about 80-100% or at least about 80%, 85%, 86%, 87%, 88%, 89%, 90%, 91%, 92%, 93%, 94%, 95%, 96%, 97%, 98%, or 99% the plasma nicotine $T_{max}$ value of a traditional cigarette.

In an aspect, provided herein is a device (e.g., an electronic nicotine delivery system such as an electronic nicotine delivery system disclosed herein) comprising a nicotine liquid formulation disclosed herein.

In an aspect, provided herein is an electronic nicotine delivery system cartridge comprising a nicotine liquid formulation disclosed herein. In embodiments, the cartridge is in a package such as a blister pack. In embodiments, the cartridge is in an electronic nicotine delivery system. In embodiments, the cartridge serves as a mouthpiece and a reservoir for the formulation. In embodiments, the cartridge is a cartomizer.

In embodiments, the aerosol produced from an electronic nicotine delivery system is produced from a single nicotine liquid formulation that is in a single reservoir contained within an electronic nicotine delivery system or a cartridge thereof.

Non-limiting examples of nicotine liquid formulations comprising one or more organic acids are disclosed in U.S. Pat. No. 9,215,895; U.S. Patent Application Publication No. 2016/0302471; and PCT International Application Publication No. WO 2018/031600, the entire contents of each of which are incorporated herein by reference.

Unless specified and depending on context, the term "nicotine" means "free base nicotine and/or protonated nicotine" (regardless of the counterion). In embodiments, the nicotine in a nicotine liquid formulation provided herein is either naturally occurring nicotine (e.g., from extract of nicotineous species such as tobacco), or synthetic nicotine. In embodiments, the nicotine is (−)-nicotine, (+)-nicotine, or a mixture thereof. In embodiments, the nicotine is employed in relatively pure form (e.g., greater than about 80% pure, 85% pure, 90% pure, 95% pure, 99% pure, 99.5% pure, or 99.9% pure by weight before it is combined with one or more other ingredients of a formulation). In embodiments, the nicotine for a formulation provided herein is "water clear" in appearance in order to avoid or minimize the formation of tarry residues during the subsequent formulation steps. In embodiments, 90-100% or at least 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% of the nicotine in a formulation is (−)-nicotine.

In embodiments, a nicotine liquid formulation includes an organic acid.

The term "organic acid" refers to an organic compound with acidic properties (e.g., by Brønsted-Lowry definition, or Lewis definition). Common organic acids are the carboxylic acids, whose acidity is associated with their carboxyl group (—COOH). A dicarboxylic acid possesses two carboxylic acid groups. The relative acidity of an organic is measured by its $pK_a$ value and one of skill in the art knows how to determine the acidity of an organic acid based on its given pKa value. The term "keto acid" as used herein, refers to organic compounds that contain a carboxylic acid group and a ketone group. Common types of keto acids include alpha-keto acids, or 2-oxoacids, such as pyruvic acid or oxaloacetic acid, having the keto group adjacent to the carboxylic acid; beta-keto acids, or 3-oxoacids, such as acetoacetic acid, having the ketone group at the second carbon from the carboxylic acid; and gamma-keto acids, or 4-oxoacids, such as levulinic acid, having the ketone group at the third carbon from the carboxylic acid. In embodiments, the organic acid is benzoic acid, oxalic acid, salicylic acid, succinic acid, sorbic acid, pyruvic acid, levulinic acid, or lactic acid.

In embodiments, the organic acid is a carboxylic acid. In embodiments, the carboxylic acid is an aliphatic acid. In embodiments, the aliphatic acid is a straight-chain aliphatic acid. In embodiments, the aliphatic acid is a branched-chain aliphatic acid. In embodiments, the aliphatic acid is an aliphatic monocarboxylic acid. In embodiments, the aliphatic acid is an aliphatic dicarboxylic acid. In embodiments, the aliphatic dicarboxylic acid is malonic acid or succinic acid. In embodiments, the carboxylic acid is an aromatic acid. In embodiments, the aromatic acid is benzoic acid or phenylacetic acid.

In embodiments, the carboxylic acid is a hydroxyacid. In embodiments, the hydroxyacid is lactic acid.

In embodiments, the organic acid is a keto acid. In embodiments, the keto acid is an alpha-keto acid. In embodiments, the alpha-keto acid is pyruvic acid or oxaloacetic acid. In embodiments, the keto acid is a beta-keto acid. In embodiments, the beta-keto acid is acetoacetic acid. In embodiments, the keto acid is a gamma-keto acid. In embodiments, the gamma-keto acid is levulinic acid.

In embodiments, the organic acid is any one or more of 2-furoic acid, acetic acid, acetoacetic acid, alpha-methylbutyric acid, ascorbic acid, benzoic acid, beta-methylvaleric acid, butyric acid, caproic acid, citric acid, formic acid, fumaric acid, glycolic acid, heptanoic acid, isobutyric acid, isovaleric acid, lactic acid, levulinic acid, malic acid, malonic acid, myristic acid, nonanoic acid, octanoic acid, oxalic acid, oxaloacetic acid, phenylacetic acid, propionic acid, pyruvic acid, succinic acid, and tartaric acid.

Non-limiting examples of organic acids in dude aromatic acids such as optionally substituted benzoic acids, hydroxyacids, heterocyclic acids, terpenoid acids, sugar acids such as the pectic acids, amino acids, cycloaliphatic acids, dicarboxylic acids, aliphatic acids, keto acids, and the like. In embodiments, a formulation includes one or more organic acids that are aliphatic acids (e.g., straight-chain and/or branched-chain aliphatic acids). In embodiments, t a formulation includes one or more organic acids that are aliphatic monocarboxylic acids such as acetic acid, propionic acid, isobutyric acid, butyric acid, or the like. In embodiments, a formulation includes one or more organic acids that are keto carboxylic acids. In embodiments, a formulation includes formic, acetic, propionic, isobutyric, butyric, alpha-methylbutyric, isovaleric, beta-methylvaleric, caproic, 2-furoic, phenylacetic, heptanoic, octanoic, nonanoic, malic, citric, oxalic, malonic, glycolic, succinic, ascorbic, tartaric, fumaric, and/or pyruvic acid. In embodiments, a formulation includes one or more $C_4$ to $C_{28}$ fatty acids, and other such acids.

In embodiments, a formulation includes one or more carboxylic acids. Non-limiting examples of carboxylic acids include monocarboxylic acids, dicarboxylic acids (organic acid containing two carboxylic acid groups), and carboxylic acids containing an aromatic group such as benzoic acids, hydroxycarboxylic acids, heterocyclic carboxylic acids, terpenoid acids, and sugar acids; such as the pectic acids, amino acids, cycloaliphatic acids, aliphatic carboxylic acids, keto carboxylic acids, and the like. In embodiments, a formulation includes one or more of formic acid, acetic acid, propionic acid, butyric acid, valeric acid, caproic acid, caprylic acid, capric acid, citric acid, lauric acid, myristic acid, palmitic acid, stearic acid, oleic acid, linoleic acid, linolenic acid, phenylacetic acid, benzoic acid, pyruvic acid, levulinic acid, tartaric acid, lactic acid, malonic acid, succinic acid, fumaric acid, gluconic acid, saccharic acid, salicyclic acid, sorbic acid, malonic acid, and malic acid. In embodiments, a formulation includes one or more of benzoic acid, pyruvic acid, salicylic acid, levulinic acid, malic acid, succinic acid, and citric acid. In embodiments, a formulation includes one or more of benzoic acid, pyruvic acid, and salicylic acid. In embodiments, a formulation includes benzoic acid. In embodiments, a formulation includes lactic acid. In embodiments, a formulation includes benzoic acid and lactic acid. In embodiments, a formulation includes at least one of benzoic acid, oxalic acid, salicylic acid, succinic acid, sorbic acid, pyruvic acid, levulinic acid, or lactic acid.

In embodiments, an organic acid used in a nicotine liquid formulation does not decompose at the operating temperature of the electronic nicotine delivery system.

In embodiments, the formulation does not include citric acid. In embodiments, the formulation does not include pyruvic acid. In embodiments, the formulation does not include malic acid. In embodiments, the formulation includes no more than 10, 9, 8, 7, 6, 5, 4, 3, 2, or 1 acid(s). In embodiments, the formulation includes no more than 10, 9, 8, 7, 6, 5, 4, 3, 2, or 1 organic acid(s). In embodiments, the formulation includes no more than 10 organic acids. In embodiments, the formulation includes no more than 9 organic acids. In embodiments, the formulation includes no more than 8 organic acids. In embodiments, the formulation includes no more than 7 organic acids. In embodiments, the formulation includes no more than 6 organic acids. In embodiments, the formulation includes no more than 5 organic acids. In embodiments, the formulation includes no more than 4 organic acids. In embodiments, the formulation includes no more than 3 organic acids. In embodiments, the formulation includes no more than 2 organic acids. In embodiments, the formulation includes only 1 organic acid. In embodiments, the formulation includes no more than 10 carboxylic acids. In embodiments, the formulation includes no more than 9 carboxylic acids. In embodiments, the formulation includes no more than 8 carboxylic acids. In embodiments, the formulation includes no more than 7 carboxylic acids. In embodiments, the formulation includes no more than 6 carboxylic acids. In embodiments, the formulation includes no more than 5 carboxylic acids. In embodiments, the formulation includes no more than 4 carboxylic acids. In embodiments, the formulation includes no more than 3 carboxylic acids. In embodiments, the formulation includes no more than 2 carboxylic acids. In embodiments, the formulation includes only 1 carboxylic acid.

In embodiments, a formulation includes an organic compound that exhibits an acid character and is capable of forming a counter ion with nicotine when in its conjugate base form. Exemplary compounds include the phenolics such as guaiacol, vanillin, protocatechualdehyde, and the like.

In embodiments, the concentration of nicotine in the nicotine liquid formulation is from about 0.5% to about 25%, wherein the concentration is of nicotine weight to total solution weight, i.e. (w/w). In embodiments, a nicotine liquid formulation has a nicotine concentration of about 1% (w/w) to about 20% (w/w). In embodiments, a nicotine liquid formulation has a nicotine concentration of about 1% (w/w) to about 18% (w/w). In embodiments, a nicotine liquid formulation has a nicotine concentration of about 1% (w/w) to about 15% (w/w). In embodiments, a nicotine liquid formulation has a nicotine concentration of about 4% (w/w) to about 12% (w/w). In embodiments, a nicotine liquid formulation has a nicotine concentration of about 1% (w/w) to about 18% (w/w), about 3% (w/w) to about 15% (w/w), or about 4% (w/w) to about 12% (w/w). In embodiments, a nicotine liquid formulation has a nicotine concentration of about 0.5% (w/w) to about 10% (w/w). In embodiments, a nicotine liquid formulation has a nicotine concentration of about 0.5% (w/w) to about 5% (w/w). In embodiments, a nicotine liquid formulation has a nicotine concentration of about 0.5% (w/w) to about 4% (w/w). In embodiments, a nicotine liquid formulation has a nicotine concentration of about 0.5% (w/w) to about 3% (w/w). In embodiments, a nicotine liquid formulation has a nicotine concentration of about 0.5% (w/w) to about 2% (w/w). In embodiments, a nicotine liquid formulation has a nicotine concentration of about 0.5% (w/w) to about 1% (w/w). In embodiments, a nicotine liquid formulation has a nicotine concentration of about 1% (w/w) to about 10% (w/w). In embodiments, a nicotine liquid formulation has a nicotine concentration of about 1% (w/w) to about 5% (w/w). In embodiments, a nicotine liquid formulation has a nicotine concentration of about 1% (w/w) to about 4% (w/w). In embodiments, a nicotine liquid formulation has a nicotine concentration of about 1% (w/w) to about 3% (w/w). In embodiments, a nicotine liquid formulation has a nicotine concentration of about 1% (w/w) to about 2% (w/w). In embodiments, a nicotine liquid formulation has a nicotine concentration of about 2% (w/w) to about 10% (w/w). In embodiments, a nicotine liquid formulation has a nicotine concentration of about 2% (w/w) to about 5% (w/w). In embodiments, a nicotine liquid formulation has a nicotine concentration of about 2% (w/w) to about 4% (w/w). In embodiments, a nicotine liquid formulation has a nicotine concentration of about 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.5%, 5.0%, 5.5%, 6.0%, 6.5%, 7.0%, 7.5%, 8.0%, 8.5%, 9.0%, 9.5%, 10%, 11%, 12%, 13%, 14%, 15%, 16%, 17%, 18%, 19%, or 20% (w/w), or more, including any increments therein. In embodiments, a nicotine liquid formulation has a nicotine liquid formulation having a nicotine concentration of about 5% (w/w). In embodiments, a nicotine liquid formulation has a nicotine concentration of about 4% (w/w). In embodiments, a nicotine liquid formulation has a nicotine concentration of about 3% (w/w). In embodiments, a nicotine liquid formulation has a nicotine concentration of about 2% (w/w). In embodiments, a nicotine liquid formulation has a nicotine concentration of about 1% (w/w). In embodiments, a nicotine liquid formulation has a nicotine concentration of about 0.5% (w/w).

In embodiments, a nicotine liquid formulation has a nicotine concentration of about 0.5% (w/w), 1% (w/w), about 2% (w/w), about 3% (w/w), about 4% (w/w), about 5% (w/w), about 6% (w/w), about 7% (w/w), about 8% (w/w), about 9% (w/w), about 10% (w/w), about 11% (w/w), about 12% (w/w), about 13% (w/w), about 14% (w/w), about 15% (w/w), about 16% (w/w), about 17% (w/w), about 18% (w/w), about 19% (w/w), or about 20% (w/w). In embodiments, a nicotine liquid formulation has a nicotine concentration from about 0.5% (w/w) to about 20% (w/w), from about 0.5% (w/w) to about 18% (w/w), from about 0.5% (w/w) to about 15% (w/w), from about 0.5% (w/w) to about 12% (w/w), from about 0.5% (w/w) to about 10% (w/w), from about 0.5% (w/w) to about 8% (w/w), from about 0.5% (w/w) to about 7% (w/w), from about 0.5% (w/w) to about 6% (w/w), from about 0.5% (w/w) to about 5% (w/w), from about 0.5% (w/w) to about 4% (w/w), from about 0.5% (w/w) to about 3% (w/w), or from about 0.5% (w/w) to about 2% (w/w). In embodiments, a nicotine liquid formulation has a nicotine concentration from about 1% (w/w) to about 20% (w/w), from about 1% (w/w) to about 18% (w/w), from about 1% (w/w) to about 15% (w/w), from about 1% (w/w) to about 12% (w/w), from about 1% (w/w) to about 10% (w/w), from about 1% (w/w) to about 8% (w/w), from about 1% (w/w) to about 7% (w/w), from about 1% (w/w) to about 6% (w/w), from about 1% (w/w) to about 5% (w/w), from about 1% (w/w) to about 4% (w/w), from about 1% (w/w) to about 3% (w/w), or from about 1% (w/w) to about 2% (w/w). In embodiments, a nicotine liquid formulation has a nicotine concentration from about 2% (w/w) to about 20% (w/w), from about 2% (w/w) to about 18% (w/w), from about 2% (w/w) to about 15% (w/w), from about 2% (w/w) to about 12% (w/w), from about 2% (w/w) to about 10% (w/w), from about 2% (w/w) to about 8% (w/w), from about 2% (w/w) to about 7% (w/w), from about 2% (w/w) to about 6% (w/w), from about 2% (w/w) to about 5% (w/w), from about 2% (w/w) to about 4% (w/w), or from about 2% (w/w) to about 3% (w/w). In embodiments, a nicotine liquid formulation has a nicotine concentration from about 3% (w/w) to about 20% (w/w), from about 3% (w/w) to about 18% (w/w), from about 3% (w/w) to about 15% (w/w), from about 3% (w/w) to about 12% (w/w), from about 3% (w/w) to about 10% (w/w), from about 3% (w/w) to about 8% (w/w), from about 3% (w/w) to about 7% (w/w), from about 3% (w/w) to about 6% (w/w), from about 3% (w/w) to about 5% (w/w), or from about 3% (w/w) to about 4% (w/w). In embodiments, a nicotine liquid formulation has a nicotine concentration from about 4% (w/w) to about 20% (w/w), from about 4% (w/w) to about 18% (w/w), from about 4% (w/w) to about 15% (w/w), from about 4% (w/w) to about 12% (w/w), from about 4% (w/w) to about 10% (w/w), from about 4% (w/w) to about 8% (w/w), from about 4% (w/w) to about 7% (w/w), from about 4% (w/w) to about 6% (w/w), or from about 4% (w/w) to about 5% (w/w). In embodiments, a nicotine liquid formulation has a nicotine concentration from about 5% (w/w) to about 20% (w/w), from about 5% (w/w) to about 18% (w/w), from about 5% (w/w) to about 15% (w/w), from about 5% (w/w) to about 12% (w/w), from about 5% (w/w) to about 10% (w/w), from about 5% (w/w) to about 8% (w/w), from about 5% (w/w) to about 7% (w/w), or from about 5% (w/w) to about 6% (w/w). In embodiments, a nicotine liquid formulation has a nicotine concentration from about 6% (w/w) to about 20% (w/w), from about 6% (w/w) to about 18% (w/w), from about 6% (w/w) to about 15% (w/w), from about 6% (w/w) to about 12% (w/w), from about 6% (w/w) to about 10% (w/w), from about 6% (w/w) to about 8% (w/w), or from about 6% (w/w) to about 7% (w/w). In embodiments, a nicotine liquid formulation has a nicotine concentration from about 2% (w/w) to about 6% (w/w). In embodiments, a nicotine liquid formulation has a nicotine concentration of about 5% (w/w).

In embodiments, the concentration of nicotine in the nicotine liquid formulation is from about 1%, 1.1%, 1.2%, 1.3%, 1.4%, 1.5%, 1.6%, or 1.7% to about 2.5%, 2.4%, 2.3%, 2.2%, 2.1%, 2.0%, 1.9%, or 1.8% (w/w). In embodiments, the concentration of nicotine in the nicotine liquid formulation is about 1%, 1.1%, 1.2%, 1.3%, 1.4%, 1.5%, 1.6%, 1.7%, 1.8%, 1.9%, 2.0%, 2.1%, 2.2%, 2.3%, 2.4%, or 2.5% (w/w).

In embodiments, the concentration of protonated nicotine in the nicotine liquid formulation is from about 0.5% (w/w) to about 25% (w/w). In embodiments, the concentration of protonated nicotine in the nicotine liquid formulation is from about 1% (w/w) to about 20% (w/w). In embodiments, the concentration of protonated nicotine in the nicotine liquid formulation is from about 1% (w/w) to about 18% (w/w). In embodiments, the concentration of protonated nicotine in the nicotine liquid formulation is from about 1% (w/w) to about 15% (w/w). In embodiments, the concentration of protonated nicotine in the nicotine liquid formulation is from about 4% (w/w) to about 12% (w/w). In embodiments, the concentration of protonated nicotine in the nicotine liquid formulation is from about 2% (w/w) to about 6% (w/w). In embodiments, the concentration of protonated nicotine in the nicotine liquid formulation is about 5% (w/w). In embodiments, the concentration of protonated nicotine in the nicotine liquid formulation is about 4% (w/w). In embodiments, the concentration of protonated nicotine in the nicotine liquid formulation is about 3% (w/w). In embodiments, the concentration of protonated nicotine in the nicotine liquid formulation is about 2% (w/w). In embodiments, the concentration of protonated nicotine in the nicotine liquid formulation is about 1% (w/w).

In embodiments, the concentration of protonated nicotine in the nicotine liquid formulation is from about 1%, 1.1%, 1.2%, 1.3%, 1.4%, 1.5%, 1.6%, or 1.7% to about 2.5%, 2.4%, 2.3%, 2.2%, 2.1%, 2.0%, 1.9%, or 1.8% (w/w). In embodiments, the concentration of protonated nicotine in the nicotine liquid formulation is about 1%, 1.1%, 1.2%, 1.3%, 1.4%, 1.5%, 1.6%, 1.7%, 1.8%, 1.9%, 2.0%, 2.1%, 2.2%, 2.3%, 2.4%, or 2.5% (w/w).

In embodiments, the concentration of organic acid in the nicotine liquid formulation is from about 0.5% to about 25%, wherein the concentration is of organic acid weight to total solution weight, i.e. (w/w). In embodiments, a nicotine liquid formulation has a organic acid concentration of about 1% (w/w) to about 20% (w/w). In embodiments, a nicotine liquid formulation has a organic acid concentration of about 1% (w/w) to about 18% (w/w). In embodiments, a nicotine liquid formulation has a organic acid concentration of about 1% (w/w) to about 15% (w/w). In embodiments, a nicotine liquid formulation has a organic acid concentration of about 4% (w/w) to about 12% (w/w). In embodiments, a nicotine liquid formulation has a organic acid concentration of about 1% (w/w) to about 18% (w/w), about 3% (w/w) to about 15% (w/w), or about 4% (w/w) to about 12% (w/w). In embodiments, a nicotine liquid formulation has a organic acid concentration of about 0.5% (w/w) to about 10% (w/w). In embodiments, a nicotine liquid formulation has a organic acid concentration of about 0.5% (w/w) to about 5% (w/w). In embodiments, a nicotine liquid formulation has a organic acid concentration of about 0.5% (w/w) to about 4% (w/w). In embodiments, a nicotine liquid formulation has a organic acid concentration of about 0.5% (w/w) to about 3% (w/w). In embodiments, a nicotine liquid formulation has a organic acid concentration of about 0.5% (w/w) to about 2% (w/w). In embodiments, a nicotine liquid formulation has a organic acid concentration of about 0.5% (w/w) to about 1% (w/w). In embodiments, a nicotine liquid formulation has a organic acid concentration of about 1% (w/w) to about 10% (w/w). In embodiments, a nicotine liquid formulation has a organic acid concentration of about 1% (w/w) to about 5% (w/w). In embodiments, a nicotine liquid formulation has a organic acid concentration of about 1% (w/w) to about 4% (w/w). In embodiments, a nicotine liquid formulation has a organic acid concentration of about 1% (w/w) to about 3% (w/w). In embodiments, a nicotine liquid formulation has a organic acid concentration of about 1% (w/w) to about 2% (w/w). In embodiments, a nicotine liquid formulation has a organic acid concentration of about 2% (w/w) to about 10% (w/w). In embodiments, a nicotine liquid formulation has a organic acid concentration of about 2% (w/w) to about 5% (w/w). In embodiments, a nicotine liquid formulation has a organic acid concentration of about 2% (w/w) to about 4% (w/w). In embodiments, a nicotine liquid formulation has a organic acid concentration of about 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.5%, 5.0%, 5.5%, 6.0%, 6.5%, 7.0%, 7.5%, 8.0%, 8.5%, 9.0%, 9.5%, 10%, 11%, 12%, 13%, 14%, 15%, 16%, 17%, 18%, 19%, or 20% (w/w), or more, including any increments therein. In embodiments, a nicotine liquid formulation has a nicotine liquid formulation having a organic acid concentration of about 5% (w/w). In embodiments, a nicotine liquid formulation has a organic acid concentration of about 4% (w/w). In embodiments, a nicotine liquid formulation has a organic acid concentration of about 3% (w/w). In embodiments, a nicotine liquid formulation has a organic acid concentration of about 2% (w/w). In embodiments, a nicotine liquid formulation has a organic acid concentration of about 1% (w/w). In embodiments, a nicotine liquid formulation has a organic acid concentration of about 0.5% (w/w).

In embodiments, a nicotine liquid formulation has a organic acid concentration of about 0.5% (w/w), 1% (w/w), about 2% (w/w), about 3% (w/w), about 4% (w/w), about 5% (w/w), about 6% (w/w), about 7% (w/w), about 8% (w/w), about 9% (w/w), about 10% (w/w), about 11% (w/w), about 12% (w/w), about 13% (w/w), about 14% (w/w), about 15% (w/w), about 16% (w/w), about 17% (w/w), about 18% (w/w), about 19% (w/w), or about 20% (w/w). In embodiments, a nicotine liquid formulation has a organic acid concentration from about 0.5% (w/w) to about 20% (w/w), from about 0.5% (w/w) to about 18% (w/w), from about 0.5% (w/w) to about 15% (w/w), from about 0.5% (w/w) to about 12% (w/w), from about 0.5% (w/w) to about 10% (w/w), from about 0.5% (w/w) to about 8% (w/w), from about 0.5% (w/w) to about 7% (w/w), from about 0.5% (w/w) to about 6% (w/w), from about 0.5% (w/w) to about 5% (w/w), from about 0.5% (w/w) to about 4% (w/w), from about 0.5% (w/w) to about 3% (w/w), or from about 0.5% (w/w) to about 2% (w/w). In embodiments, a nicotine liquid formulation has a organic acid concentration from about 1% (w/w) to about 20% (w/w), from about 1% (w/w) to about 18% (w/w), from about 1% (w/w) to about 15% (w/w), from about 1% (w/w) to about 12% (w/w), from about 1% (w/w) to about 10% (w/w), from about 1% (w/w) to about 8% (w/w), from about 1% (w/w) to about 7% (w/w), from about 1% (w/w) to about 6% (w/w), from about 1% (w/w) to about 5% (w/w), from about 1% (w/w) to about 4% (w/w), from about 1% (w/w) to about 3% (w/w), or from about 1% (w/w) to about 2% (w/w). In embodiments, a nicotine liquid formulation has a organic acid concentration from about 2% (w/w) to about 20% (w/w), from about 2% (w/w) to about 18% (w/w), from about 2% (w/w) to about 15% (w/w), from about 2% (w/w) to about 12% (w/w), from about 2% (w/w) to about 10% (w/w), from about 2% (w/w) to about 8% (w/w), from about 2% (w/w) to about 7% (w/w), from about 2% (w/w) to about 6% (w/w), from about 2% (w/w) to about 5% (w/w), from about 2% (w/w) to about 4% (w/w), or from about 2% (w/w) to about 3% (w/w). In embodiments, a nicotine liquid formulation has a organic acid concentration from about 3% (w/w) to about 20% (w/w), from about 3% (w/w) to about 18% (w/w), from about 3% (w/w) to about 15% (w/w), from about 3% (w/w) to about 12% (w/w), from about 3% (w/w) to about 10% (w/w), from about 3% (w/w) to about 8% (w/w), from about 3% (w/w) to about 7% (w/w), from about 3% (w/w) to about 6% (w/w), from about 3% (w/w) to about 5% (w/w), or from about 3% (w/w) to about 4% (w/w). In embodiments, a nicotine liquid formulation has a organic acid concentration from about 4% (w/w) to about 20% (w/w), from about 4% (w/w) to about 18% (w/w), from about 4% (w/w) to about 15% (w/w), from about 4% (w/w) to about 12% (w/w), from about 4% (w/w) to about 10% (w/w), from about 4% (w/w) to about 8% (w/w), from about 4% (w/w) to about 7% (w/w), from about 4% (w/w) to about 6% (w/w), or from about 4% (w/w) to about 5% (w/w). In embodiments, a nicotine liquid formulation has a organic acid concentration from about 5% (w/w) to about 20% (w/w), from about 5% (w/w) to about 18% (w/w), from about 5% (w/w) to about 15% (w/w), from about 5% (w/w) to about 12% (w/w), from about 5% (w/w) to about 10% (w/w), from about 5% (w/w) to about 8% (w/w), from about 5% (w/w) to about 7% (w/w), or from about 5% (w/w) to about 6% (w/w). In embodiments, a nicotine liquid formulation has a organic acid concentration from about 6% (w/w) to about 20% (w/w), from about 6% (w/w) to about 18% (w/w), from about 6% (w/w) to about 15% (w/w), from about 6% (w/w) to about 12% (w/w), from about 6% (w/w) to about 10% (w/w), from about 6% (w/w) to about 8% (w/w), or from about 6% (w/w) to about 7% (w/w). In embodiments, a nicotine liquid formulation has a organic acid concentration from about 2% (w/w) to about 6% (w/w). In embodiments, a nicotine liquid formulation has a organic acid concentration of about 5% (w/w).

In embodiments, the concentration of organic acid in the nicotine liquid formulation is from about 1%, 1.1%, 1.2%, 1.3%, 1.4%, 1.5%, 1.6%, or 1.7% to about 2.5%, 2.4%, 2.3%, 2.2%, 2.1%, 2.0%, 1.9%, or 1.8% (w/w). In embodiments, the concentration of organic acid in the nicotine liquid formulation is about 1%, 1.1%, 1.2%, 1.3%, 1.4%, 1.5%, 1.6%, 1.7%, 1.8%, 1.9%, 2.0%, 2.1%, 2.2%, 2.3%, 2.4%, or 2.5% (w/w).

Unless specified otherwise with respect to concentrations of nicotine (e.g., total nicotine, free base nicotine, and/or protonated nicotine) in a nicotine liquid formulation, the term "about" in the context of a numerical value or range means±10% of the numerical value or range recited or claimed, unless the context requires a more limited range. In each instance in which a numerical value or range is preceded by the term "about" in this description, the specific numerical value or range without the term "about" is also disclosed. For example, a disclosure of "about 1%" is also a disclosure of "1%." Where a numerical range is provided, all integers within that range, and tenths thereof, are also disclosed. For example, "0.5% to 5%" is a disclosure of 0.5%, 0.6%, 0.7%, 0.8%, 0.9%, 1%, 1.1%, etc. up to and including 5%.

In embodiments, the pH of the nicotine liquid formulation is less than 7.0. In embodiments, the pH of the formulation is from about 2.5 to about 6.5. In embodiments, the pH of the formulation is from about 3 to about 6.5. In embodiments, the pH of the formulation is from about 4 to about 6.5. In embodiments, the pH of the formulation is from about 5 to about 6.5. In embodiments, the pH of the formulation is from about 6 to about 6.5. In embodiments, the pH of the formulation is from about 3 to about 5.5. In embodiments, the pH of the formulation is from about 3.5 to about 5.5. In embodiments, the pH of the formulation is about 2.5, 3, 3.5, 4, 4.5, 5, 5.5, 6, or 6.5.

In embodiments, a formulation may include various stoichiometric ratios and/or molar ratios of acid to nicotine, acidic functional groups to nicotine, and acidic functional group hydrogens to nicotine. In embodiments, the molar ratio of the nicotine to acid (nicotine:acid) is 1:1, 1:2, 1:3, 1:4, 2:3, 2:5, 2:7, 3:4, 3:5, 3:7, 3:8, 3:10, 3:11, 4:5, 4:7, 4:9, 4:10, 4:11, 4:13, 4:14, 4:15, 5:6, 5:7, 5:8, 5:9, 5:11, 5:12, 5:13, 5:14, 5:16, 5:17, 5:18, or 5:19. In embodiments, the molar ratio of the acid to nicotine (acid:nicotine) is 1:1, 1:2, 1:3, 1:4, 2:3, 2:5, 2:7, 3:4, 3:5, 3:7, 3:8, 3:10, 3:11, 4:5, 4:7, 4:9, 4:10, 4:11, 4:13, 4:14, 4:15, 5:6, 5:7, 5:8, 5:9, 5:11, 5:12, 5:13, 5:14, 5:16, 5:17, 5:18, or 5:19. In embodiments, the ratio is the ratio of nicotine to one acid in a formulation. In embodiments, the ratio is the ratio of nicotine to all acids in a formulation. In embodiments, the ratio is the ratio of nicotine to all organic acids in a formulation. In embodiments, the molar ratio of the nicotine to acid in the formulation is 1:1, 1:2, 1:3, or 1:4. In embodiments, the molar ratio of acid to nicotine in the formulation is about 0.25:1, about 0.3:1, about 0.4:1, about 0.5:1, about 0.6:1, about 0.7:1, about 0.8:1, about 0.9:1, about 1:1, about 1.2:1, about 1.4:1, about 1.6:1, about 1.8:1, about 2:1, about 2.2:1, about 2.4:1, about 2.6:1, about 2.8:1, about 3:1, about 3.2:1, about 3.4:1, about 3.6:1, about 3.8:1, or about 4:1. In embodiments, the molar ratio of acidic functional groups to nicotine in the formulation is about 0.25:1, about 0.3:1, about 0.4:1, about 0.5:1, about 0.6:1, about 0.7:1, about 0.8:1, about 0.9:1, about 1:1, about 1.2:1, about 1.4:1, about 1.6:1, about 1.8:1, about 2:1, about 2.2:1, about 2.4:1, about 2.6:1, about 2.8:1, about 3:1, about 3.2:1, about 3.4:1, about 3.6:1, about 3.8:1, or about 4:1. In embodiments, the molar ratio of acidic functional group hydrogens to nicotine in the formulation is about 0.25:1, about 0.3:1, about 0.4:1, about 0.5:1, about 0.6:1, about 0.7:1, about 0.8:1, about 0.9:1, about 1:1, about 1.2:1, about 1.4:1, about 1.6:1, about 1.8:1, about 2:1, about 2.2:1, about 2.4:1, about 2.6:1, about 2.8:1, about 3:1, about 3.2:1, about 3.4:1, about 3.6:1, about 3.8:1, or about 4:1. In embodiments, the molar ratio of acid to nicotine in the aerosol is about 0.25:1, about 0.3:1, about 0.4:1, about 0.5:1, about 0.6:1, about 0.7:1, about 0.8:1, about 0.9:1, about 1:1, about 1.2:1, about 1.4:1, about 1.6:1, about 1.8:1, about 2:1, about 2.2:1, about 2.4:1, about 2.6:1, about 2.8:1, about 3:1, about 3.2:1, about 3.4:1, about 3.6:1, about 3.8:1, or about 4:1. In embodiments, the molar ratio of acidic functional groups to nicotine in the aerosol is about 0.25:1, about 0.3:1, about 0.4:1, about 0.5:1, about 0.6:1, about 0.7:1, about 0.8:1, about 0.9:1, about 1:1, about 1.2:1, about 1.4:1, about 1.6:1, about 1.8:1, about 2:1, about 2.2:1, about 2.4:1, about 2.6:1, about 2.8:1, about 3:1, about 3.2:1, about 3.4:1, about 3.6:1, about 3.8:1, or about 4:1. In embodiments, the molar ratio of acidic functional group hydrogens to nicotine in the aerosol is about 0.25:1, about 0.3:1, about 0.4:1, about 0.5:1, about 0.6:1, about 0.7:1, about 0.8:1, about 0.9:1, about 1:1, about 1.2:1, about 1.4:1, about 1.6:1, about 1.8:1, about 2:1, about 2.2:1, about 2.4:1, about 2.6:1, about 2.8:1, about 3:1, about 3.2:1, about 3.4:1, about 3.6:1, about 3.8:1, or about 4:1.

In embodiments, the nicotine is protonated. In embodiments, the number or moles of organic acid functional groups is equal to or greater than the molar amount of nicotine. In embodiments, the number or moles of organic acid functional groups is equal to the molar amount of nicotine.

In embodiments, the number or moles of organic acid functional groups is greater than the molar amount of nicotine.

In embodiments, the number or moles of organic acid functional groups is from about 1.1 times greater to about 3.0 times greater than the molar amount of nicotine. In embodiments, the number of organic acid functional groups is from about 1.5 times greater to about 2.2 times greater than the molar amount of nicotine.

In embodiments, the amount of or moles of excess organic acid functional groups is about 1.1 times greater, or about 1.2 times greater, or about 1.3 times greater, or about 1.4 times greater, or about 1.5 times greater, or about 1.6 times greater, or about 1.7 times greater, or about 1.8 times greater, or about 2 times greater, or about 2.1 times greater, or about 2.2 times greater, or about 2.3 times greater, or about 2.4 times greater, or about 2.5 times greater, or about 2.6 times greater, or about 2.7 times greater, or about 2.8 times greater, or about 2.9 times greater, or about 3.0 times greater, etc., than the molar amount of nicotine present in the formulation. In embodiments, the excess amount or moles of organic acid functional groups, provide less harshness upon inhalation to a user relative to a control formulation.

In embodiments, the molar ratio of organic acid to nicotine is about 0.5:1. In embodiments, the molar ratio of organic acid to nicotine is about 0.6:1. In embodiments, the molar ratio of organic acid to nicotine is about 0.7:1. In embodiments, the molar ratio of organic acid to nicotine is about 0.8:1. In embodiments, the molar ratio of organic acid to nicotine is about 0.9:1. In embodiments, the molar ratio of organic acid to nicotine is about 1.0:1. In embodiments, the molar ratio of organic acid to nicotine is about 1.1:1. In embodiments, the molar ratio of organic acid to nicotine is about 1.2:1. In embodiments, the molar ratio of organic acid to nicotine is about 1.3:1. In embodiments, the molar ratio of organic acid to nicotine is about 1.4:1. In embodiments, the molar ratio of organic acid to nicotine is about 1.5:1. In embodiments, the molar ratio of organic acid to nicotine is about 1.6:1. In embodiments, the molar ratio of organic acid to nicotine is about 1.7:1. In embodiments, the molar ratio of organic acid to nicotine is about 1.8:1. In embodiments, the molar ratio of organic acid to nicotine is about 1.9:1. In embodiments, the molar ratio of organic acid to nicotine is about 2.0:1. In embodiments, the molar ratio of organic acid to nicotine is about 3:1. In embodiments, the molar ratio of organic acid to nicotine is about 4:1. In embodiments, the molar ratio of organic acid to nicotine is about 5:1. In embodiments, the molar ratio of organic acid to nicotine is about 6:1. In embodiments, the molar ratio of organic acid to nicotine is about 7:1. In embodiments, the molar ratio of organic acid to nicotine is about 8:1. In embodiments, the molar ratio of organic acid to nicotine is about 9:1. In embodiments, the molar ratio of organic acid to nicotine is about 10:1. In embodiments, the molar ratio of organic acid to nicotine is about 11:1. In embodiments, the molar ratio of organic acid to nicotine is about 12:1. In embodiments, the molar ratio of organic acid to nicotine is about 13:1. In embodiments, the molar ratio of organic acid to nicotine is about 14:1. In embodiments, the molar ratio of organic acid to nicotine is about 15:1. In embodiments, the molar ratio of organic acid to nicotine is about 16:1. In embodiments, the molar ratio of organic acid to nicotine is about 17:1. In embodiments, the molar ratio of organic acid to nicotine is about 18:1. In embodiments, the molar ratio of organic acid to nicotine is about 19:1. In embodiments, the molar ratio of organic acid to nicotine is about 20:1.

In embodiments, the molar ratio of organic acid to nicotine is at least 0.5:1. In embodiments, the molar ratio of organic acid to nicotine is at least 0.6:1. In embodiments, the molar ratio of organic acid to nicotine is at least 0.7:1. In embodiments, the molar ratio of organic acid to nicotine is at least 0.8:1. In embodiments, the molar ratio of organic acid to nicotine is at least 0.9:1. In embodiments, the molar ratio of organic acid to nicotine is at least 1.0:1. In embodiments, the molar ratio of organic acid to nicotine is at least 1.1:1. In embodiments, the molar ratio of organic acid to nicotine is at least 1.2:1. In embodiments, the molar ratio of organic acid to nicotine is at least 1.3:1. In embodiments, the molar ratio of organic acid to nicotine is at least 1.4:1. In embodiments, the molar ratio of organic acid to nicotine is at least 1.5:1. In embodiments, the molar ratio of organic acid to nicotine is at least 1.6:1. In embodiments, the molar ratio of organic acid to nicotine is at least 1.7:1. In embodiments, the molar ratio of organic acid to nicotine is at least 1.8:1. In embodiments, the molar ratio of organic acid to nicotine is at least 1.9:1. In embodiments, the molar ratio of organic acid to nicotine is at least 2.0:1. In embodiments, the molar ratio of organic acid to nicotine is at least 3:1. In embodiments, the molar ratio of organic acid to nicotine is at least 4:1. In embodiments, the molar ratio of organic acid to nicotine is at least 5:1. In embodiments, the molar ratio of organic acid to nicotine is at least 6:1. In embodiments, the molar ratio of organic acid to nicotine is at least 7:1. In embodiments, the molar ratio of organic acid to nicotine is at least 8:1. In embodiments, the molar ratio of organic acid to nicotine is at least 9:1. In embodiments, the molar ratio of organic acid to nicotine is at least 10:1. In embodiments, the molar ratio of organic acid to nicotine is at least 11:1. In embodiments, the molar ratio of organic acid to nicotine is at least 12:1. In embodiments, the molar ratio of organic acid to nicotine is at least 13:1. In embodiments, the molar ratio of organic acid to nicotine is at least 14:1. In embodiments, the molar ratio of organic acid to nicotine is at least 15:1. In embodiments, the molar ratio of organic acid to nicotine is at least 16:1. In embodiments, the molar ratio of organic acid to nicotine is at least 17:1. In embodiments, the molar ratio of organic acid to nicotine is at least 18:1. In embodiments, the molar ratio of organic acid to nicotine is at least 19:1. In embodiments, the molar ratio of organic acid to nicotine is at least 20:1.

Nicotine is an alkaloid molecule that has two basic nitrogens. It may occur in different states of protonation. Nicotine is "protonated" if at least one of the two nitrogens is covalently bound to a proton. Protonated nicotine includes monoprotonated nicotine, diprotonated nicotine, and combinations thereof. If one nitrogen is protonated, then the nicotine is "monoprotonated" nicotine. If two nitrogens are protonated, then the nicotine is "diprotonated" nicotine. If no protonation exists, nicotine is referred to as the "free base" nicotine. In embodiments, when nicotine is combined with a sufficient amount of acid, the nicotine becomes protonated. Once protonated, the nicotine positively charged and the formulation may further include a counter ion. In embodiments, the counter ion is the conjugate base of the acid. For example, where the acid is benzoic acid, the counter ion may be benzoate, thereby forming nicotine benzoate.

In embodiments, different nicotine liquid formulations produce varying degrees of increase in a nicotine-related biological effect (e.g., a faster rise in heart rate). In embodiments, different nicotine liquid formulations produce varying degrees of satisfaction, stimulation, nicotine delivery, and/or heart rate increase in an individual. In embodiments, the extent of protonation of the nicotine effects satisfaction, stimulation, nicotine delivery, and/or heart rate such that more protonation is more satisfying as compared to less protonation. In embodiments, nicotine, for example in the formulation, and/or aerosol is monoprotonated. In embodiments, nicotine, for example in the formulation, and/or aerosol is diprotonated. In embodiments, nicotine, for example in the formulation, and/or aerosol is exists in more than one protonation state, e.g., an equilibrium of monoprotonated and diprotonated nicotine. In embodiments, the extent of protonation of nicotine is dependent upon the ratio of nicotine:acid used in the formulation. In embodiments, the extent of protonation of nicotine is dependent upon the solvent. In embodiments, the extent of protonation of nicotine has not been determined.

In embodiments, a liquid carrier includes a liquid solvent or medium in which a protonated nicotine is soluble (e.g., at ambient conditions, such as 25 degrees Celsius) such that the protonated nicotine does not form a solid precipitate. Examples include, but are not limited to, glycerol, propylene glycol, trimethylene glycol, water, ethanol and the like, as well as combinations thereof. In embodiments, the liquid carrier includes a ratio of propylene glycol and vegetable glycerin. In embodiments, the liquid carrier includes 10% to 70% of propylene glycol and 90% to 30% of vegetable glycerin. In embodiments, the liquid carrier includes 20% to 50% of propylene glycol and 80% to 50% of vegetable glycerin. In embodiments, the liquid carrier includes 30% propylene glycol and 70% vegetable glycerin. In embodiments, the liquid carrier is completely propylene glycol or vegetable glycerin. In embodiments, the liquid carrier includes another aerosol forming agent similar to propylene glycol, glycerin, or other glycols or the like, or any combination thereof.

In embodiments, heating an amount of a nicotine liquid formulation produces a aerosol, wherein at least about 50% of acid in the amount is in the aerosol. In embodiments, at least about 90% of the nicotine in the amount is in the aerosol. In embodiments, at least about 50%, at least about 60%, at least about 70%, at least about 80%, at least about 90%, at least 95%, or at least about 99% of the acid in the amount is in the aerosol. In embodiments, at least about 50% to about 99% of the acid in the amount is in the aerosol. In embodiments, at least about 50% to about 95% of the acid in the amount is in the aerosol. In embodiments, at least about 50% to about 90% of the acid in the amount is in the aerosol. In embodiments, at least about 50% to about 80% of the acid in the amount is in the aerosol. In embodiments, at least about 50% to about 70% of the acid in the amount is in the aerosol. In embodiments, at least about 50% to about 60% of the acid in the amount is in the aerosol. In embodiments, at least about 60% to about 99% of the acid in the amount is in the aerosol. In embodiments, at least about 60% to about 95% of the acid in the amount is in the aerosol. In embodiments, at least about 60% to about 90% of the acid in the amount is in the aerosol. In embodiments, at least about 60% to about 80% of the acid in the amount is in the aerosol. In embodiments, at least about 60% to about 70% of the acid in the amount is in the aerosol. In embodiments, at least about 70% to about 99% of the acid in the amount is in the aerosol. In embodiments, at least about 70% to about 95% of the acid in the amount is in the aerosol. In embodiments, at least about 70% to about 90% of the acid in the amount is in the aerosol. In embodiments, at least about 70% to about 80% of the acid in the amount is in the aerosol. In embodiments, at least about 50%, at least about 60%, at least about 70%, at least about 80%, at least about 90%, at least 95%, or at least about 99% of the nicotine in the amount is in the aerosol. In embodiments, at least about 50% to about 99% of the nicotine in the amount is in the aerosol. In embodiments, at least about 50% to about 95% of the nicotine in the amount is in the aerosol. In embodiments, at least about 50% to about 90% of the nicotine in the amount is in the aerosol. In embodiments, at least about 50% to about 80% of the nicotine in the amount is in the aerosol. In embodiments, at least about 50% to about 70% of the nicotine in the amount is in the aerosol. In embodiments, at least about 50% to about 60% of the nicotine in the amount is in the aerosol. In embodiments, at least about 60% to about 99% of the nicotine in the amount is in the aerosol. In embodiments, at least about 60% to about 95% of the nicotine in the amount is in the aerosol. In embodiments, at least about 60% to about 90% of the nicotine in the amount is in the aerosol. In embodiments, at least about 60% to about 80% of the nicotine in the amount is in the aerosol. In embodiments, at least about 60% to about 70% of the nicotine in the amount is in the aerosol. In embodiments, at least about 70% to about 99% of the nicotine in the amount is in the aerosol. In embodiments, at least about 70% to about 95% of the nicotine in the amount is in the aerosol. In embodiments, at least about 70% to about 90% of the nicotine in the amount is in the aerosol. In embodiments, at least about 70% to about 80% of the nicotine in the amount is in the aerosol.

In embodiments, the aerosol is delivered in particles small enough to be delivered through the oral or nasal cavity and to a user's lungs, for example the alveoli of a user's lungs. In embodiments, the aerosol particles are sized (e.g., have a diameter of) from about 0.1 microns to about 5 microns, from about 0.1 microns to about 4.5 microns, from about 0.1 microns to about 4 microns, from about 0.1 microns to about 3.5 microns, from about 0.1 microns to about 3 microns, from about 0.1 microns to about 2.5 microns, from about 0.1 microns to about 2 microns, from about 0.1 microns to about 1.5 microns, from about 0.1 microns to about 1 microns, from about 0.1 microns to about 0.9 microns, from about 0.1 microns to about 0.8 microns, from about 0.1 microns to about 0.7 microns, from about 0.1 microns to about 0.6 microns, from about 0.1 microns to about 0.5 microns, from about 0.1 microns to about 0.4 microns, from about 0.1 microns to about 0.3 microns, from about 0.1 microns to about 0.2 microns, from about 0.2 microns to about 5 microns, from about 0.2 microns to about 4.5 microns, from about 0.2 microns to about 4 microns, from about 0.2 microns to about 3.5 microns, from about 0.2 microns to about 3 microns, from about 0.2 microns to about 2.5 microns, from about 0.2 microns to about 2 microns, from about 0.2 microns to about 1.5 microns, from about 0.2 microns to about 1 microns, from about 0.2 microns to about 0.9 microns, from about 0.2 microns to about 0.8 microns, from about 0.2 microns to about 0.7 microns, from about 0.2 microns to about 0.6 microns, from about 0.2 microns to about 0.5 microns, from about 0.2 microns to about 0.4 microns, from about 0.2 microns to about 0.3 microns, from about 0.3 microns to about 5 microns, from about 0.3 microns to about 4.5 microns, from about 0.3 microns to about 4 microns, from about 0.3 microns to about 3.5 microns, from about 0.3 microns to about 3 microns, from about 0.3 microns to about 2.5 microns, from about 0.3 microns to about 2 microns, from about 0.3 microns to about 1.5 microns, from about 0.3 microns to about 1 microns, from about 0.3 microns to about 0.9 microns, from about 0.3 microns to about 0.8 microns, from about 0.3 microns to about 0.7 microns, from about 0.3 microns to about 0.6 microns, from about 0.3 microns to about 0.5 microns, from about 0.3 microns to about 0.4, from about 0.4 microns to about 5 microns, from about 0.4 microns to about 4.5 microns, from about 0.4 microns to about 4 microns, from about 0.4 microns to about 3.5 microns, from about 0.4 microns to about 3 microns, from about 0.4 microns to about 2.5 microns, from about 0.4 microns to about 2 microns, from about 0.4 microns to about 1.5 microns, from about 0.4 microns to about 1 microns, from about 0.4 microns to about 0.9 microns, from about 0.4 microns to about 0.8 microns, from about 0.4 microns to about 0.7 microns, from about 0.4 microns to about 0.6 microns, from about 0.4 microns to about 0.5 microns, from about 0.5 microns to about 5 microns, from about 0.5 microns to about 4.5 microns, from about 0.5 microns to about 4 microns, from about 0.5 microns to about 3.5 microns, from about 0.5 microns to about 3 microns, from about 0.5 microns to about 2.5 microns, from about 0.5 microns to about 2 microns, from about 0.5 microns to about 1.5 microns, from about 0.5 microns to about 1 microns, from about 0.5 microns to about 0.9 microns, from about 0.5 microns to about 0.8 microns, from about 0.5 microns to about 0.7 microns, from about 0.5 microns to about 0.6 microns, from about 0.6 microns to about 5 microns, from about 0.6 microns to about 4.5 microns, from about 0.6 microns to about 4 microns, from about 0.6 microns to about 3.5 microns, from about 0.6 microns to about 3 microns, from about 0.6 microns to about 2.5 microns, from about 0.6 microns to about 2 microns, from about 0.6 microns to about 1.5 microns, from about 0.6 microns to about 1 microns, from about 0.6 microns to about 0.9 microns, from about 0.6 microns to about 0.8 microns, from about 0.6 microns to about 0.7 microns, from about 0.8 microns to about 5 microns, from about 0.8 microns to about 4.5 microns, from about 0.8 microns to about 4 microns, from about 0.8 microns to about 3.5 microns, from about 0.8 microns to about 3 microns, from about 0.8 microns to about 2.5 microns, from about 0.8 microns to about 2 microns, from about 0.8 microns to about 1.5 microns, from about 0.8 microns to about 1 microns, from about 0.8 microns to about 0.9 microns, from about 0.9 microns to about 5 microns, from about 0.9 microns to about 4.5 microns, from about 0.9 microns to about 4 microns, from about 0.9 microns to about 3.5 microns, from about 0.9 microns to about 3 microns, from about 0.9 microns to about 2.5 microns, from about 0.9 microns to about 2 microns, from about 0.9 microns to about 1.5 microns, from about 0.9 microns to about 1 microns, from about 1 microns to about 5 microns, from about 1 microns to about 4.5 microns, from about 1 microns to about 4 microns, from about 1 microns to about 3.5 microns, from about 1 microns to about 3 microns, from about 1 microns to about 2.5 microns, from about 1 microns to about 2 microns, from about 1 microns to about 1.5 microns.

In embodiments, an amount of nicotine liquid formulation provided to the heater includes a volume or a mass. In embodiments, the amount is quantified "per puff." In embodiments, the amount includes a volume of about 1 µL, about 2 µL, about 3 µL, about 4 µL, about 5 µL, about 6 µL, about 7 µL, about 8 µL, about 9 µL, about 10 µL, about 15 µL, about 20 µL, about 25 µL, about 30 µL, about 35 µL, about 40 µL, about 45 µL, about 50 µL, about 60 µL, about 70 µL, about 80 µL, about 90 µL, about 100 µL, or greater than about 100 µL. In embodiments, the amount includes a mass of about 1 mg, about 2 mg, about 3 mg, about 4 mg, about 5 mg, about 6 mg, about 7 mg, about 8 mg, about 9 mg, about 10 mg, about 15 mg, about 20 mg, about 25 mg, about 30 mg, about 35 mg, about 40 mg, about 45 mg, about 50 mg, about 60 mg, about 70 mg, about 80 mg, about 90 mg, about 100 mg, or greater than about 100 mg.

In embodiments, nicotine in aerosol from a device provided herein is delivered (e.g., absorbed) faster than nicotine in the smoke from a traditional cigarette, such that less nicotine is needed in the aerosol. In embodiments, one puff of the aerosol has less nicotine than one puff from a traditional cigarette. In embodiments, the one puff of the aerosol is the first, second, third, fourth, fifth, sixth, seventh, eighth, ninth, or tenth puff from a cartridge-containing device disclosed herein when the device is fully charged and a new cartridge is used. In embodiments, the one puff from the traditional cigarette is the first, second, third, fourth, fifth, sixth, seventh, eighth, ninth, or tenth puff from the traditional cigarette after the cigarette is first lit. In embodiments, a "puff" is about a 40 ml, 45 ml, 50 ml, 55 ml, 60 ml, 65 ml, 70 ml, 75 ml, or 80 ml volume of aerosol (in the case of a device disclosed herein) or smoke (in the case of a traditional cigarette). In embodiments, the puff is drawn from the device or traditional cigarette over a 1-5 second period of time. In embodiments, the puff is drawn from the device or traditional cigarette over a 2-3 second period of time. In embodiments, the puff is drawn from the device or traditional cigarette over a 2-3 second period of time. In embodiments, the puff is drawn grom the device or traditional cigarette over a period of about 1, 2, 3, 4, or 5 seconds. In embodiments, the puff is drawn grom the device or traditional cigarette over a period of about 1 seconds. In embodiments, the puff is drawn grom the device or traditional cigarette over a period of about 2 seconds. In embodiments, the puff is drawn grom the device or traditional cigarette over a period of about 3 seconds. In embodiments, the puff is drawn grom the device or traditional cigarette over a period of about 4 seconds. In embodiments, the puff is drawn from the device or traditional cigarette over a period of about 5 seconds. In embodiments, less nicotine is in a puff from a device disclosed herein compared to a traditional cigarette, wherein the puff from the device has a volume of about 70 ml and is drawn from the device over about a 3 second period of time, and wherein the puff from the traditional cigarette has a volume of about 55 ml and is drawn from the traditional cigarette over about a 2 second period of time. In embodiments, a 40-80 ml puff (e.g., 40 ml, 45 ml, 50 ml, 55 ml, 60 ml, 65 ml, 70 ml, 75 ml, or 80 ml) drawn from a device disclosed herein over a period of about 1-5 seconds (e.g., about 1, 1.5, 2, 2.5, 3, 3.5, 4, 4.5, 5, 2-5, 2-4, 2-3, or 1-3 seconds) has about 0.5-1 mg of nicotine. In embodiments, the puff has about 0.5, 0.55, 0.6, 0.65, 0.75, 0.80, 0.85, 0.95, or 1 mg of nicotine. In embodiments, the puff has 0.5-0.75 mg of nicotine. In embodiments, the puff has about 0.75-1 mg nicotine. In embodiments, the puff has 0.65-0.85 mg nicotine.

In embodiments, more of the nicotine in aerosol from a device provided herein is delivered (e.g., absorbed) by a user compared to nicotine in the smoke from a traditional cigarette, such that less nicotine is exhaled by the user. As used herein, the "exhaled nicotine amount" is the amount of nicotine that exit's a user's airways when the user first exhales after inhaling a puff. In embodiments, a user's exhaled nicotine amount is less when using a device disclosed herein compared to when using a traditional cigarette. In embodiments, the exhaled nicotine amount when using a device as disclosed herein is at least about 5%, 10%, 15%, 20%, 25%, 30%, 35%, 40%, 45%, 50%, 55%, 60%, 65%, 70%, 75%, 80%, or 95% less than when using a traditional cigarette. In embodiments, when a user inhales aerosol produced by a device provided herein, at least about 75, 80, 85, 90, 95, 96, 97, 98, or 99% of the nicotine remains within the user (i.e., is not exhaled). In embodiments, when a user inhales aerosol produced by a device provided herein, about 80-100%, 80-90%, 85-95%, 90-100%, 95-100%, 90-95%, 90-99%, 95-99% of the nicotine is not exhaled. In embodiments, when a user inhales aerosol produced by a device provided herein, none of the nicotine is exhaled. In embodiments, a device provided herein is more effective at controlling the dose of nicotine per puff than a traditional cigarette.

In embodiments, a nicotine liquid formulation may comprise one or more flavorants.

In embodiments, the flavor of the constituent acid used in the formulation is a consideration in choosing the acid. In embodiments, a suitable acid has minimal or no toxicity to humans in the concentrations used. In embodiments, a suitable acid is compatible with the electronic nicotine delivery system components it contacts or could contact at the concentrations used. That is, such acid does not degrade or otherwise react with the electronic nicotine delivery system components it contacts or could contact. In embodiments, the odor of the constituent acid used to protonate nicotine is a consideration in choosing a suitable acid. In embodiments, the concentration of protonated nicotine in the carrier may affect the satisfaction of the user. In embodiments, the flavor of the formulation is adjusted by changing the acid. In embodiments, the flavor of the formulation is adjusted by adding exogenous flavorants. In embodiments, an unpleasant tasting or smelling acid is used in minimal quantities to mitigate such characteristics. In embodiments, exogenous pleasant smelling or tasting acid is added to the formulation. Non-limiting examples of organic acids that can provide flavor and aroma to the aerosol at certain levels include acetic acid, oxalic acid, malic acid, isovaleric acid, lactic acid, citric acid, phenylacetic acid, and myristic acid.

In embodiments, the amount of nicotine aerosol (e.g., comprising protonated nicotine) inhaled may be user-determined. In embodiments, the user may, for example, modify the amount of nicotine by adjusting his or her inhalation strength.

In embodiments, the electronic nicotine delivery system does not deliver an increased level of oxygen to the user, e.g., compared to ambient oxygen levels. In embodiments, the electronic nicotine delivery system does not comprise pressurized oxygen gas, or a chemical store of oxygen for inclusion in the aerosol. In embodiments, the aerosol comprises, consists essentially of, or consists of aerosolized nicotine liquid formulation, optionally in combination with ambient air.

Terminology

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present.

Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments and implementations only and is not intended to be limiting. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

Spatially relative terms, such as "forward", "rearward", "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings provided herein.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the teachings herein. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the claims.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A method of manufacturing a vaporizer cartridge, comprising:
    filling a first part of a volume of a mold with a first material, wherein the volume defines the vaporizer cartridge and the first part defines a reservoir housing of the vaporizer cartridge, the reservoir housing comprising a reservoir wall;
    filling a second part of the volume of the mold with a second material, wherein the second part defines a mouthpiece of the vaporizer cartridge and is separate from the first part, the mouthpiece comprising a mouthpiece wall;
    curing the first material and the second material;
    contacting a first end of the reservoir wall with a second end of the mouthpiece wall; and
    laser welding the first end of the reservoir wall to the second end of the mouthpiece wall such that an inner reservoir surface of the reservoir wall is continuous and co-planar with an inner mouthpiece surface of the mouthpiece wall, wherein the reservoir wall and the mouthpiece wall define at least a part of a reservoir chamber for containing a vaporizable material.

2. The method of claim 1, wherein an outer reservoir surface of the reservoir wall is co-planar with an outer mouthpiece surface of the mouthpiece wall.

3. The method of claim 1, wherein the first material is translucent.

4. The method of claim 1, wherein the second material is opaque.

5. The method of claim 1, wherein the first part includes a stepped portion defining a stop feature along the reservoir housing.

6. The method of claim 5, wherein the stop feature is shaped to prevent insertion of the vaporizer cartridge into a vaporizer body past the stepped portion.

7. The method of claim 5, wherein the stop feature includes an increase in a cross section of the reservoir housing.

8. The method of claim 2, wherein a wall thickness of the vaporizer cartridge is substantially the same along the reservoir housing and the mouthpiece.

9. The method of claim 1, further comprising:
    filling a second mold with a third material, wherein the second mold defines an air tube assembly.

10. The method of claim 9, further comprising laser welding the air tube assembly to at least one of the reservoir housing and the mouthpiece.

11. The method of claim 10, further comprising coupling a seal to a port of the air tube assembly thereby fluidically sealing a reservoir chamber in the reservoir housing.

12. The method of claim 11, further comprising delivering a vaporizable material to the reservoir chamber.

13. A vaporizer cartridge for coupling to a vaporizer body to form a vaporizer, comprising:
    a reservoir housing defining a first part of a reservoir chamber, the reservoir chamber configured to contain a vaporizable material, the reservoir housing comprising a reservoir wall;
    a mouthpiece comprising a mouthpiece wall, the mouthpiece wall coupled to the reservoir wall of the reservoir housing such that an inner reservoir surface of the reservoir wall is continuous and co-planar with an inner mouthpiece surface of the mouthpiece wall, wherein the mouthpiece wall defines a second part of a reservoir chamber for containing a vaporizable material; and
    an air tube assembly comprising:
        a wick housing portion configured to position a wicking element and a heating element in a vaporization chamber for vaporizing the vaporizable material in the vaporization chamber;
        a tubing portion comprising a part of an airflow pathway that extends through the vaporization chamber and the mouthpiece thereby allowing vaporized vaporizable material to be inhaled by a user; and
        a filter housing portion configured to position a filter adjacent the mouthpiece.

14. The vaporizer cartridge of claim 13, wherein the air tube assembly is made out of a single molded part.

15. The vaporizer cartridge of claim 13, wherein the tubing portion is made out of metal.

16. The vaporizer cartridge of claim 15, wherein the filter housing portion and the wick housing portion is made out of a plastic material.

17. The vaporizer cartridge of claim 13, wherein an outer reservoir surface of the reservoir wall is co-planar with an outer mouthpiece surface of the mouthpiece wall.

18. The vaporizer cartridge of claim 13, wherein a first end of the reservoir wall is laser welded to a second end of the mouthpiece wall.

* * * * *